United States Patent
Foody et al.

(10) Patent No.: US 12,338,406 B2
(45) Date of Patent: Jun. 24, 2025

(54) METHOD AND SYSTEM FOR PRODUCING A FUEL FROM BIOGAS

(71) Applicant: Iogen Corporation, Ottawa (CA)

(72) Inventors: Brian Foody, Ottawa (CA); Patrick J. Foody, Ottawa (CA); John Dechman, Ottawa (CA)

(73) Assignee: Iogen Corporation, Ottawa (CA)

( * ) Notice: Subject to any disclaimer, the term of this patent is extended or adjusted under 35 U.S.C. 154(b) by 0 days.

(21) Appl. No.: 18/592,334

(22) Filed: Feb. 29, 2024

(65) Prior Publication Data

US 2024/0209272 A1 Jun. 27, 2024

Related U.S. Application Data

(63) Continuation of application No. 17/597,110, filed as application No. PCT/CA2020/050936 on Jul. 6, 2020, now Pat. No. 11,946,006.

(60) Provisional application No. 62/872,007, filed on Jul. 9, 2019.

(51) Int. Cl.
*C10L 3/10* (2006.01)
*C12M 1/00* (2006.01)
*C12M 1/107* (2006.01)

(52) U.S. Cl.
CPC ............ *C10L 3/10* (2013.01); *C12M 21/04* (2013.01); *C12M 47/18* (2013.01)

(58) Field of Classification Search
CPC ......... C10L 3/10; C12M 21/04; C12M 47/18; C12M 47/20; Y02E 50/30
See application file for complete search history.

(56) References Cited

U.S. PATENT DOCUMENTS

| | | | |
|---|---|---|---|
| 4,380,242 | A | 4/1983 | Bresie et al. |
| 4,677,827 | A | 7/1987 | Shenoy et al. |
| 5,570,729 | A | 11/1996 | Mutter |
| 5,603,360 | A | 2/1997 | Teel |
| 6,112,528 | A | 9/2000 | Rigby |
| 6,932,121 | B1 | 8/2005 | Shivers, III |

(Continued)

FOREIGN PATENT DOCUMENTS

| CA | 2842759 | 2/2013 |
|---|---|---|
| CA | 2820733 | 7/2017 |

(Continued)

OTHER PUBLICATIONS

"Good Practices and Innovations in the Biogas Industry", European Biogas Association, Jan. 2018 (downloaded Aug. 28, 2019), in 100 pages. URL: http://european-biogas.eu/wp-content/uploads/2018/02/Success-Stories-EBA-2018.pdf.

(Continued)

*Primary Examiner* — Ellen M McAvoy
(74) *Attorney, Agent, or Firm* — Knobbe Martens Olson & Bear LLP

(57) ABSTRACT

A method for producing a fuel includes transporting one or more pressure vessels containing pressurized biogas from a first location to a second location, and removing biogas from the one or more pressure vessels at the second location. The fuel production process is improved by controlling the decanting flow rate to provide a total decant time greater than 30-40 minutes, by actively heating biogas contained within the one or more pressure vessels, or some combination thereof.

20 Claims, 14 Drawing Sheets

(56) References Cited

U.S. PATENT DOCUMENTS

| | | | |
|---|---|---|---|
| 7,691,182 B1 | 4/2010 | Muradov et al. |
| 7,731,779 B2 | 6/2010 | Palumbo |
| 8,007,567 B2 | 8/2011 | Roe et al. |
| 8,373,305 B2 | 2/2013 | Adam et al. |
| 8,404,025 B2 | 3/2013 | Frisbie et al. |
| 8,549,877 B2 | 10/2013 | Santos |
| 8,658,026 B2 | 2/2014 | Foody et al. |
| 8,753,854 B2 | 6/2014 | Foody |
| 8,833,088 B2 | 9/2014 | Bayliff et al. |
| 8,945,373 B2 | 2/2015 | Foody |
| 8,999,036 B2 | 4/2015 | Pierce |
| 9,040,271 B2 | 5/2015 | Foody |
| 9,108,894 B1 | 8/2015 | Foody et al. |
| 9,145,300 B1 | 9/2015 | Foody |
| 9,222,048 B1 | 12/2015 | Foody |
| 9,234,627 B2 | 1/2016 | Cajiga et al. |
| 9,243,190 B2 | 1/2016 | Patience et al. |
| 9,506,605 B2 | 11/2016 | Paget et al. |
| 9,514,464 B2 | 12/2016 | Foody |
| 9,535,045 B2 | 1/2017 | Gerhold |
| 9,605,286 B2 | 3/2017 | Foody |
| 9,625,097 B2 | 4/2017 | Bayliff et al. |
| 9,625,099 B2 | 4/2017 | Ding |
| 9,644,792 B2 | 5/2017 | Moszkowski et al. |
| 9,863,581 B2 | 1/2018 | Santos et al. |
| 9,969,949 B1 | 5/2018 | Foody et al. |
| 10,093,540 B2 | 10/2018 | Foody |
| 10,132,447 B2 | 11/2018 | Whiteman et al. |
| 10,183,267 B2 | 1/2019 | Day et al. |
| 10,202,622 B2 | 2/2019 | Foody et al. |
| 10,421,663 B2 | 9/2019 | Foody |
| 10,487,282 B2 | 11/2019 | Foody et al. |
| 10,619,173 B2 | 4/2020 | Foody et al. |
| 10,640,793 B2 | 5/2020 | Foody et al. |
| 10,723,621 B2 | 7/2020 | Foody |
| 10,760,024 B2 | 9/2020 | Foody et al. |
| 10,894,968 B2 | 1/2021 | Foody et al. |
| 10,968,151 B1 | 4/2021 | Whitmore |
| 10,981,784 B2 | 4/2021 | Foody |
| 11,220,470 B2 | 1/2022 | Whitmore |
| 11,299,686 B2 | 4/2022 | Foody et al. |
| 11,434,509 B2 | 9/2022 | Foody et al. |
| 11,708,313 B2 | 7/2023 | Whitmore |
| 11,746,301 B2 | 9/2023 | Foody et al. |
| 11,760,630 B2 | 9/2023 | Foody |
| 11,827,916 B2 | 11/2023 | Foody et al. |
| 11,946,001 B2 | 4/2024 | Foody |
| 11,946,006 B2 | 4/2024 | Foody et al. |
| 12,241,036 B2 | 3/2025 | Foody et al. |
| 2003/0225169 A1 | 12/2003 | Yetman |
| 2006/0213370 A1 | 9/2006 | Leonard et al. |
| 2007/0157804 A1 | 7/2007 | McManus et al. |
| 2008/0134754 A1 | 6/2008 | Funk |
| 2008/0209916 A1 | 9/2008 | White |
| 2010/0000153 A1 | 1/2010 | Kurkjian et al. |
| 2010/0108567 A1 | 5/2010 | Medoff |
| 2011/0084020 A1 | 4/2011 | Ott |
| 2012/0308989 A1 | 12/2012 | Barclay et al. |
| 2013/0183705 A1 | 7/2013 | Barclay et al. |
| 2013/0224808 A1 | 8/2013 | Bell et al. |
| 2014/0227751 A1 | 8/2014 | Datta et al. |
| 2014/0349360 A1 | 11/2014 | Zhang et al. |
| 2014/0370559 A1 | 12/2014 | Oakley et al. |
| 2015/0101671 A1 | 4/2015 | Paget et al. |
| 2015/0211684 A1 | 7/2015 | Santos et al. |
| 2015/0345708 A1 | 12/2015 | Sloan et al. |
| 2016/0178128 A1 | 6/2016 | Le Bruchec et al. |
| 2016/0245459 A1 | 8/2016 | Grimmer et al. |
| 2016/0247183 A1 | 8/2016 | Foody |
| 2016/0281927 A1 | 9/2016 | Bjorn et al. |
| 2016/0290563 A1* | 10/2016 | Diggins .................. F17C 7/00 |
| 2017/0074583 A1 | 3/2017 | Tremblay |
| 2017/0130901 A1 | 5/2017 | Sloan et al. |
| 2017/0241592 A1 | 8/2017 | Whiteman et al. |
| 2017/0304769 A1 | 10/2017 | Bigeard et al. |
| 2018/0079672 A1 | 3/2018 | Meyer |
| 2018/0094772 A1 | 4/2018 | Santos et al. |
| 2018/0112142 A1 | 4/2018 | Foody et al. |
| 2018/0138528 A1 | 5/2018 | Komiya |
| 2018/0155649 A1 | 6/2018 | Gerhold |
| 2019/0001263 A1 | 1/2019 | Prince |
| 2019/0030482 A1 | 1/2019 | Ding |
| 2019/0144890 A1 | 5/2019 | Subbian et al. |
| 2019/0185884 A1 | 6/2019 | Foody |
| 2019/0224617 A1 | 7/2019 | Mitariten |
| 2019/0262770 A1 | 8/2019 | Thygesen |
| 2020/0318896 A1 | 10/2020 | Prince et al. |
| 2021/0055046 A1 | 2/2021 | Prince |
| 2021/0060486 A1 | 3/2021 | Prince |
| 2021/0094894 A1 | 4/2021 | Whitmore |
| 2021/0155864 A1 | 5/2021 | Foody et al. |
| 2021/0172677 A1 | 6/2021 | Terrien et al. |
| 2021/0275961 A1 | 9/2021 | Foody et al. |
| 2021/0317377 A1 | 10/2021 | Foody et al. |
| 2021/0324282 A1 | 10/2021 | Foody et al. |
| 2023/0053930 A1 | 2/2023 | Foody et al. |
| 2023/0295523 A1 | 9/2023 | Foody |
| 2024/0025739 A1 | 1/2024 | Foody |
| 2024/0123399 A1 | 4/2024 | Buckenham |
| 2025/0084334 A1 | 3/2025 | Foody et al. |

FOREIGN PATENT DOCUMENTS

| | | |
|---|---|---|
| DE | 10 2013 011 289 | 1/2015 |
| EP | 0 207 277 | 1/1990 |
| EP | 3 085 766 | 10/2016 |
| EP | 4 043 089 | 8/2022 |
| WO | WO 2010/006910 | 1/2010 |
| WO | WO 2011/101137 A1 | 8/2011 |
| WO | WO 2013/021140 | 2/2013 |
| WO | WO 2017/195103 | 11/2017 |
| WO | WO 2018/144328 | 8/2018 |
| WO | WO 2019/185315 | 10/2019 |
| WO | WO 2020/010430 | 1/2020 |
| WO | WO 2020/010431 | 1/2020 |
| WO | WO 2020/041857 | 3/2020 |
| WO | WO 2021/003564 | 1/2021 |
| WO | WO 2021/142528 | 7/2021 |
| WO | WO 2022/147610 | 7/2022 |

OTHER PUBLICATIONS

"IPCC Fourth Assessment Report: Climate Change 2007, 5.3.1.3 Alternative fuels—AR4 WGIII Chapter 5: Transport and its infrastructure", IPCC, accessed Oct. 14, 2020, in 5 pages. URL: https://archive.ipcc.ch/publications_and_data/ar4/wg3/en/ch5s5-3-1-3.html.

Beilstein et al., "Ethanol producers need to reduce their CI score—and quickly", Ethanol Producer Magazine, Oct. 31, 2019, in 5 pages. URL: http://ethanolproducer.com/articles/16668/ethanol-producers-need-to-reduce-their-ci-scoreundefinedand-quickly.

Biswas et al., "Biofuels and Their Production Through Different Catalytic Routes", Chemical and Biochemical Engineering Quarterly, Apr. 2017, vol. 31, pp. 47-62.

Hakawati et al., "What is the most energy efficient route for biogas utilization: Heat, electricity or transport?", Applied Energy, Nov. 2017, vol. 206, pp. 1076-1087.

Heijstra et al., "Gas Fermentation: Cellular Engineering Possibilities and Scale Up", Microbial Cell Factories, Apr. 2017, vol. 16, in 11 pages.

Hengeveld et al., "Biogas infrastructures from farm to regional scale, prospects of biogas transport grids", Biomass and Bioenergy, Mar. 2016, vol. 86, pp. 43-52.

Hengeveld et al., "When does decentralized production of biogas and centralized upgrading and injection into the natural gas grid make sense?", Biomass and Bioenergy, Jun. 2014, vol. 67, pp. 363-371.

Hjort, A. et al., "Transport Alternatives for Biogas", BioMil AB, Nov. 2012, in 35 pages.

(56) References Cited

OTHER PUBLICATIONS

Hovland, J., "Kompresjon av ra biogass", Tel-Tek, dated Jun. 1, 2017, in 24 pages.
Hovland et al., "Compression and Transport of Raw Biogas", Sintef Tel-tek, 2019, in 32 pages.
Hovland, J. et al., "Compression of raw biogas—A feasibility study", Tel-Tek, Apr. 2017, Report No. 2217020-1, in 12 pages.
Kapoor, R. et al., "Seventh Framework Programme Theme Energy", 7 Cooperation, downloaded on Aug. 27, 2019, in 59 pages. URL: http://www.valorgas.soton.ac.uk/Deliverables/120825_VALORGAS_241334_D5-2_rev[0].pdf.
Krich K. et al., "Chapter 4—Storage and Transportation of Biogas Biomethane", Biomethane from Dairy Waste: A Sourcebook for the Production and Use of Renewable Natural Gas in California, 2005 (downloaded on Aug. 23, 2019), in 10 pages. URL: http://www.suscon.org/pdfs/cowpower/biomethaneSourcebook/Chapter_4.pdf.
Li et al., "Capturing CO2 from biogas plants", Energy Procedia, Jul. 2017, vol. 114, pp. 6030-6035.
Munoth, K. et al., "Models for Decanting Gaseous Fuel Tanks: Simulations with GFSSP Thermal Model", Mechanical (and Materials) Engineering—Dissertations, University of Nebraska-Lincoln, Dec. 2016, in 133 pages.
Privat, R. et al., "Chapter 15—Predicting the Phase Equilibria of Carbon Dioxide Containing Mixtures Involved in CCS Processes Using the PPR78 Model," CO2 Sequestration and Valorization, Mar. 2014, in 20 pages.
Rufford et al., "The removal of CO2 and N2 from natural gas: A review of conventional and emerging process technologies", Journal of Petroleum Science and Engineering, vol. 94-95, Sep. 2012, pp. 123-154.
Scholwin et al., "Biogas for Road Vehicles: Technology Brief", IRENA Mar. 2017 (Mar. 2017), in 62 pages.
Schill, S., "California Carbon Check", Ethanol Producer Magazine, Jan. 23, 2019, in 3 pages. URL: http://www.ethanolproducer.com/articles/15888/california-carbon-check.
Stafford et al., "Biofuels Technology", United Nations University, WIDER Working Paper 2017/87, Apr. 2017, in 25 pages.
Torresani, M. et al., "Renewable Natural Gas Delivery Options. Getting your RNG to Market", Tetra Tech, Mar. 2018, Swanapalooza, Denver, Colorado, in 21 pages.
Unnasch, S., "GHG Emissions Reductions due to the RFS2: A 2018 Update", Life Cycle Associates, Feb. 6, 2019, in 19 pages.
Vitu, S et al., "Predicting the phase equilibria of CO2 + hydrocarbon systems with the PPR78 model (PR EOS and kij calculated through a group contribution method)", Journal of Supercritical Fluids, May 2008, vol. 45, pp. 1-26.
Wang, Z., "Positioning your plant to maximize the opportunity created by low carbon fuel markets", ACE EcoEngineers, Aug. 16, 2018, in 27 pages.
Chinese Office Action in CN Application No. 201980045125.7 dated May 27, 2022.
European Office Action in EP Application No. 19833590.3 dated Mar. 3, 2022.
European Office Action in EP Application No. 19833450.0 dated May 3, 2022.
European Office Action in EP Application No. 19853629.4 dated May 20, 2022.
International Search Report and Written Opinion mailed Oct. 18, 2019 for PCT Application No. PCT/CA2019/000104, filed Jul. 9, 2019.
International Preliminary Report on Patentability issued Jan. 21, 2021 for PCT Application No. PCT/CA2019/000104, filed Jul. 9, 2019.
International Search Report and Written Opinion mailed Sep. 16, 2019 for PCT Application No. PCT/CA2019/000103, filed Jul. 9, 2019.
International Preliminary Report on Patentability issued Jan. 21, 2021 for PCT Application No. PCT/CA2019/000103, filed Jul. 9, 2019.
International Search Report and Written Opinion mailed Mar. 17, 2022 for PCT Application No. PCT/CA2021/051845, filed Mar. 17, 2022.
International Search Report and Written Opinion mailed Nov. 8, 2019 for PCT Application No. PCT/CA2019/000122, filed Aug. 23, 2019.
International Preliminary Report on Patentability issued Mar. 11, 2021 for PCT Application No. PCT/CA2019/000122, filed Aug. 23, 2019.
Invitation to Pay Additional Fees mailed Sep. 2, 2020 for PCT Application No. PCT/CA2020/050936, filed Jul. 6, 2020.
International Search Report and Written Opinion mailed Oct. 22, 2020 for PCT Application No. PCT/CA2020/050936, filed Jul. 6, 2020.
International Preliminary Report on Patentability issued Jan. 20, 2022 for PCT Application No. PCT/CA2020/050936, filed Jul. 6, 2020.
Office Action for U.S. Appl. No. 17/258,607, dated Nov. 26, 2021.
Office Action for U.S. Appl. No. 17/258,607, dated May 12, 2022.
Office Action for U.S. Appl. No. 17/271,014, dated Jul. 11, 2024.
Chinese Office Action in CN Application No. 201980045125.7 dated Jan. 28, 2023.
Chinese Office Action in CN Application No. 201980045125.7 dated Apr. 28, 2023.
International Preliminary Report on Patentability issued Jul. 4, 2023 for PCT Application No. PCT/CA2021/051845.
Advisory Action for U.S. Appl. No. 17/258,607, dated Jul. 22, 2022.
Advisory Action for U.S. Appl. No. 17/258,607, dated Sep. 1, 2022.
Office Action for U.S. Appl. No. 17/258,607, dated Oct. 27, 2022.
Office Action for U.S. Appl. No. 17/258,607, dated Mar. 17, 2022.
Office Action for U.S. Appl. No. 17/258,607, dated Apr. 13, 2023.
Office Action for U.S. Appl. No. 17/258,607, dated Jan. 5, 2024.
Restriction Requirement for U.S. Appl. No. 17/258,711 dated Dec. 29, 2023.
Office Action for U.S. Appl. No. 17/652,868, dated Oct. 6, 2022.
Office Action for U.S. Appl. No. 17/652,868, dated Mar. 6, 2023.
Notice of Allowance for U.S. Appl. No. 17/652,868, dated Apr. 19, 2023.
Canadian Office Action in CA Application No. 3,102,390 dated Mar. 1, 2024.
Canadian Office Action in CA Application No. 3,102,417 dated Feb. 2, 2024.
Canadian Office Action in CA Application No. 3,112,339 dated Mar. 20, 2024.
Canadian Office Action in CA Application No. 3,145,848 dated Mar. 1, 2024.
European Office Action in EP Application No. 20836871.2 dated Apr. 2, 2024.
Office Action for U.S. Appl. No. 17/258,607, dated Jun. 6, 2024.
Office Action for U.S. Appl. No. 17/258,711, dated Jun. 6, 2024.
Restriction Requirement for U.S. Appl. No. 17/142,537, dated Jun. 12, 2024.
Canadian Notice of Allowance in CA Application No. 3,145,848 dated Mar. 13, 2025.

* cited by examiner

METHOD AND SYSTEM FOR PRODUCING A FUEL FROM BIOGAS

CROSS-REFERENCE TO RELATED APPLICATIONS

This application is a continuation of U.S. patent application Ser. No. 17/597,110, filed on Dec. 27, 2021, which claims priority to PCT/CA2020/050936, filed Jul. 6, 2020, which claims the benefit of U.S. Provisional Application No. 62/872,007, filed Jul. 9, 2019, both of which are incorporated by reference herein in their entireties.

TECHNICAL FIELD

The present disclosure relates to a method and/or system for producing a fuel from biogas, and in particular, relates to a method and system for producing a fuel from biogas that includes transporting raw or partially purified biogas in one or more pressure vessels.

BACKGROUND

Biogas, which is a mixture of several gases, is typically produced by the breakdown of organic matter in low oxygen conditions. In particular, it is typically produced by the anaerobic digestion of organic matter (e.g., manure, sewage sludge, municipal solid waste, biodegradable waste, biodegradable feedstock, etc.).

Biogas contains methane ($CH_4$), a flammable gas that is used as a fuel and is the main constituent of natural gas (NG). However, since biogas may have a significant non-methane content, it is generally viewed as a low value fuel (e.g., has a low energy density relative to NG). While biogas may be combusted in stationary engines (e.g., in a combined heat and power (CHP) unit), it is generally not suitable for use in the transportation sector without being upgraded to renewable natural gas (RNG) and/or converted to another transportation fuel.

Using biogas to produce a transportation fuel is advantageous because the resulting transportation fuel may be considered renewable or to have renewable content, and/or may qualify for fuel credits (e.g., associated with reduced carbon intensity). The use of the resulting transportation fuel is advantageous because it may displace the use of fossil transportation fuels (e.g., NG, diesel, etc.). However, producing a transportation fuel from biogas may be cost prohibitive, particularly for small-scale biogas producers.

For example, consider a process where biogas is used to produce RNG. RNG, which may be produced by upgrading biogas, is substantially interchangeable with NG and may be used by any vehicle that uses NG. Unfortunately, since biogas upgrading typically requires separating $CH_4$ from $CO_2$ and/or separating $CH_4$ from $N_2$, the cost of upgrading biogas, and thus producing RNG, may be high. Moreover, the cost of producing RNG is typically dependent on the scale and location of a project. For example, the RNG supply costs (e.g., in $/kJ) for a small-scale farm-based AD project can be twice that of a larger landfill project. This may be a significant deterrent to small-scale biogas upgrading.

In addition, there may be significant deterrents to transporting biogas. Unlike RNG which can be transported using any method used to deliver NG, the significant $CO_2$ content of raw biogas can make its delivery technically and/or economically challenging. For example, since raw biogas generally cannot be injected into an existing NG distribution system, a dedicated biogas pipeline may be necessary. This may require significant investment costs, and moreover, may not be economically and/or physically feasible for some small-scale biogas producers (e.g., a remote AD facility). Furthermore, while NG may be transported as compressed natural gas (CNG), or as liquefied natural gas (LNG), the significant $CO_2$ content of raw biogas may make these methods impractical. For example, CNG may be transported at pressures between 2900-3600 psig (~20-25 MPa). However, the significant $CO_2$ content of raw biogas makes it more challenging and/or costly to compress and transport raw biogas.

As a result of these economic challenges, biogas has been conventionally limited to combustion on-site in suitable furnaces and/or engines for the production of heat, electricity, and/or motive power (e.g., in a CHP unit) in order to supply or supplant the facilities utility requirements.

SUMMARY

The present disclosure describes methods of producing a fuel from biogas, wherein the biogas is transported as pressurized gas in one or more pressure vessels. More specifically, the present disclosure describes various improvements to the loading, transportation, and/or unloading of the biogas that promote producing a transportation fuel from biogas. For example, these improvements may improve the economics of the fuel production process, may improve efficiency, and/or may reduce technical complications related to transporting biogas.

In accordance with one aspect of the instant invention there is provided a method of producing a fuel comprising: a) filling a pressure vessel system with biogas; b) transporting the pressure vessel system containing the biogas from a first location to a second location; and c) unloading the biogas transported in step (b), said unloading comprising removing the biogas from the pressure vessel system at the second location, said removing comprising: (i) controlling a flow rate to provide a total decant time greater than 40 minutes; or (ii) actively heating biogas contained within a pressure vessel of the pressure vessel system; or (iii) a combination of (i) and (ii), and d) feeding the biogas unloaded in step (c) into a biogas upgrading system, a fuel production process, or a combination thereof, wherein step (i), or (ii), or (iii) is performed such that a temperature of biogas within the pressure vessel system, in degrees Celsius, is greater than $$\frac{P-2550}{40}$$

as the biogas is unloaded, where P is the pressure of the biogas in the pressure vessel system in psig.

In accordance with one aspect of the instant invention there is provided a method of producing a renewable fuel comprising: a) filling a pressure vessel system with biogas to a pressure greater than 1000 psig (6.9 MPa) and less than 2000 psig (13.8 MPa), the pressure vessel system having a nominal pressure rating greater than 1000 psig at 21° C., said filling comprising filling the pressure vessel system such that a density of the biogas therein is greater than the design density of natural gas; b) transporting the pressure vessel system containing pressurized biogas from a first location to a second location; c) unloading biogas from the pressure vessel system at the second location, said unloading comprising controlling a flow rate to provide a total decant time greater than 1 hour; and d) feeding the biogas unloaded in step (c) into a biogas upgrading system, a fuel production process, or a combination thereof.

In accordance with one aspect of the instant invention there is provided a method of producing a renewable fuel comprising: a) filling a pressure vessel system with biogas to a pressure greater than 1000 psig (6.9 MPa) and less than 2000 psig (13.8 MPa), the pressure vessel system having a nominal pressure rating greater than 1000 psig at 21° C., said filling comprising filling the pressure vessel system such that a density of the biogas therein is greater than the design density of natural gas; b) transporting pressure vessel system containing pressurized biogas from a first location to a second location; c) unloading biogas from the pressure vessel system at the second location, said unloading comprising heating gas within a pressure vessel of the pressure vessel system; and d) feeding the biogas unloaded in step (c) into a biogas upgrading system, a fuel production process, or a combination thereof.

In accordance with one aspect of the instant invention there is provided a method of producing a renewable fuel comprising: a) identifying a plurality sites, each site comprising a source of biogas; b) at each site, (i) removing one or more components from the biogas to provide partially purified biogas, wherein said one or more components includes water, hydrogen sulfide, carbon dioxide or any combination thereof; (ii) feeding the partially purified biogas into a pressure vessel system to a pressure greater than 1000 psig (6.9 MPa); c) transporting the pressure vessel system containing the partially purified biogas from each site to a central processing site; d) unloading partially purified biogas from each pressure vessel system at the central processing site, wherein said unloading comprises heating gas within at least one pressure vessel in one of the pressure vessel systems, and controlling a flow rate of gas leaving each pressure vessel system to provide a total decant time greater than 30 minutes; and, e) feeding the biogas unloaded in step (c) into a biogas upgrading system, a fuel production process, or a combination thereof.

In accordance with one aspect of the instant invention there is provided a method of producing a renewable fuel comprising: a) filling a pressure vessel system with biogas, said pressure vessel system comprising a plurality of vertically oriented gas cylinders; b) transporting the pressure vessel system containing the biogas from a first location to a second location; c) unloading biogas from the pressure vessel system at the second location, said unloading comprising removing the biogas through an orifice disposed in a bottom third of one of the gas cylinders; and d) feeding the biogas unloaded in step (c) into a biogas upgrading system, a fuel production process, or a combination thereof.

In accordance with one aspect of the instant invention there is provided a method of producing a renewable fuel comprising: a) receiving a plurality of pressure vessel systems, said plurality of pressure vessel systems comprising a first pressure vessel system containing a first biogas having a first density and a second pressure vessel system containing a second biogas having a second density; b) providing fluid communication between the first pressure vessel system and a first valve and between the second pressure vessel system and a second valve, each of said first and second valves in fluid communication with a same pressure let down system; c) unloading the first and second biogases from the first and second pressure vessel systems, respectively, wherein said unloading comprises actuating the first and second valves such that the pressure let down system receives biogas from the first and second pressure vessel systems in succession before the first biogas is fully unloaded from the first pressure vessel system; and d) feeding at least a portion of first and second biogases unloaded in step (c) into a biogas upgrading system, a fuel production process, or a combination thereof.

In accordance with one aspect of the instant invention there is provided a method of producing a fuel comprising: a) filling a pressure vessel system with biogas such that a density of the biogas is greater than a design density of natural gas; b) transporting the pressure vessel system containing the biogas from a first location to a second location; c) unloading the biogas transported in step (b), said unloading comprising removing the biogas from the pressure vessel system at the second location, said removing comprising: (i) controlling a flow rate to provide a total decant time greater than 1 hour; (ii) actively heating biogas contained within the pressure vessel system; or (iii) a combination of (i) and (ii), and d) feeding the biogas unloaded in step (c) into a biogas upgrading system, a fuel production process, or a combination thereof, wherein step (i), (ii), or (iii) is performed such that a temperature of biogas within the pressure vessel system, in degrees Celsius, is greater than $$\frac{P - 2550}{40}$$

as the biogas is unloaded, when P is greater than 0 psig and below 1500 psig, where P is the pressure of the biogas in the pressure vessel system in psig.

In accordance with one aspect of the instant invention there is provided a method of producing a renewable fuel comprising: a) receiving a plurality of pressure vessel systems, said plurality of pressure vessel systems comprising a first pressure vessel system containing a first biogas having a first density and a second pressure vessel system containing a second biogas having a second density; b) providing fluid communication between the first pressure vessel system and a first valve and between the second pressure vessel system and a second valve, each of said first and second valves in fluid communication with a pressure let down system; c) unloading the first and second biogases from the first and second pressure vessel systems, respectively, wherein said unloading comprises actuating the first and second valves such that while unloading each of the first and second pressure vessel systems a first portion of the respective biogas is provided at a pressure above 500 psig (3.4 MPa), and a second portion is provided at a pressure below 500 psig; and d) feeding the first and second biogases unloaded in step (c) into a biogas upgrading system, a fuel production process, or a combination thereof.

DETAILED DESCRIPTION

Figure 1:
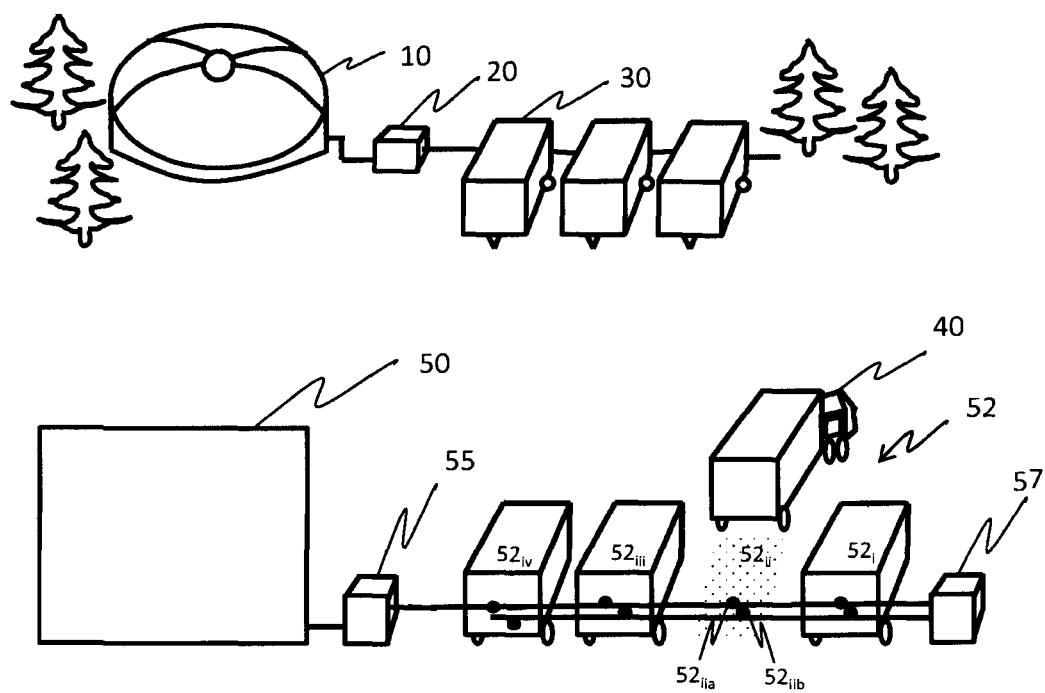
FIG. 1 is a schematic diagram of a system wherein biogas is transported from a biogas source to a receiving station.

Certain exemplary embodiments of the invention now will be described in more detail, with reference to the drawings, in which like features are identified by like reference numerals. The invention may, however, be embodied in many different forms and should not be construed as limited to the embodiments set forth herein. The terminology used herein is for the purpose of describing certain embodiments only and is not intended to be limiting of the invention. For example, as used herein, the singular forms "a," "an," and "the" may include plural references unless the context clearly dictates otherwise. The terms "comprises", "comprising", "including", and/or "includes", as used herein, are intended to mean "including but not limited to." The term "and/or", as used herein, is intended to refer to either or both of the elements so conjoined. The phrase "at least one" in reference to a list of one or more elements, is intended to refer to at least one element selected from any one or more of the elements in the list of elements, but not necessarily including at least one of each and every element specifically listed within the list of elements. Thus, as a non-limiting example, the phrase "at least one of A and B" may refer to at least one A with no B present, at least one B with no A present, or at least one A and at least one B in combination. In the context of describing the combining of components by the "addition" or "adding" of one component to another, or the separating of components by the "removal" or "removing" of one component from another, those skilled in the art will understand that the order of addition/removal is not critical (unless stated otherwise). The terms "remove", "removing", and "removal", with reference to one or more impurities, contaminants, and/or constituents of biogas, includes partial removal. The terms "cause" or "causing", as used herein, may include arranging or bringing about a specific result (e.g., a withdrawal of a gas), either directly or indirectly, or to play a role in a series of activities through commercial arrangements such as a written agreement, verbal agreement, or contract. The term "associated with", as used herein with reference to two elements (e.g., a fuel credit associated with the transportation fuel), is intended to refer to the two elements being connected with each other, linked to each other, related in some way, dependent upon each other in some way, and/or in some relationship with each other. The terms "first", "second", etc., may be used to distinguish one element from another, and these elements should not be limited by these terms. Unless defined otherwise, all technical and scientific terms used herein have the same meanings as commonly understood by one of ordinary skill in the art.

Virtual pipeline systems have been proposed to deliver natural gas (NG) to areas not serviced by an existing NG pipeline system. For example, a virtual pipeline system may include a mother station at which NG may be loaded onto trucks and one or more daughter stations, at which the NG may be decanted (i.e., removed). In order to ensure the economic viability of such a system (e.g., decrease the cost per energy unit delivered), it can be important to increase the amount of gas delivered per truck. For example, CNG is often transported at pressures between 2900 and 3600 psig (~20-25 MPa). This is typically much higher than the pressure of NG pipeline systems.

Relative to pipeline NG, the loading, transport, and decanting of pressurized biogas may be challenging. For a given pressure, temperature, and volume, raw biogas or partially purified biogas may be denser than pipeline NG. This higher density can complicate the loading, transport, and/or decanting of pressurized biogas (i.e., raw or partially purified). For example, consider the transport of pressurized biogas by truck. In many jurisdictions, when transporting CNG, the total truck weight (e.g., truck plus payload) is not allowed to exceed a predetermined maximum weight. For this reason, the pressure vessel(s) of a CNG trailer may be designed with a total volume and/or nominal pressure rating that keeps the maximum filled weight below a certain limit. However, at a given temperature, a pressure vessel containing raw biogas at some pressure will typically weigh more than it would if it contained pipeline NG at the same pressure and temperature. Accordingly, a CNG trailer having a nominal pressure rating of 3600 psig (24.8 MPa), may not be able to transport raw biogas at 3600 psig (e.g., during the loading step it may top out in weight before 3600 psig is reached). This reduces the economic feasibility of transporting biogas.

In addition, the composition of biogas (i.e., raw or partially purified) may complicate the loading, transport, and/or decanting of biogas. For example, raw or partially purified biogas may have a significant $CO_2$ content. This $CO_2$ content may make it less energy efficient to compress the biogas (e.g., relative to pipeline NG) and/or may cause the biogas to undergo a phase change at temperatures that pipeline NG does not. In general, phase changes are undesirable (e.g., may restrict gas flow through tubing, may cause material fatigue in the equipment, and/or may affect the composition of the biogas as it is decanted). The risk of phase change may be more of a concern when gas at high pressure is decanted quickly as the pressure drop may result in very low temperatures (e.g., −75° C.).

In accordance with one embodiment, the process of producing a fuel from biogas (i.e., raw or partially purified) is improved by transporting biogas in a pressure vessel system such that the mass of biogas of a given composition is increased and/or such that the risk of phase changes within the pressure vessel system is reduced during the decanting process.

For example, consider a fuel production process that makes use of the transportation system illustrated in FIG. 1. In this case, the fuel may be produced by collecting biogas from a biogas source 10, subjecting the biogas to an optional partial purification 20, loading the biogas into one or more pressure vessels (e.g., pressure vessel system 30), and transporting the one or more pressure vessels to a destination (e.g., receiving station 52) by vehicle 40.

Biogas

The term "biogas", as used herein, refers to a gas mixture that contains methane produced from the anaerobic digestion of organic matter. Some examples of organic matter that may be used to produce biogas include, but are not limited to, manure, agricultural by-products, energy crops, wastewater sludge, industrial waste, and municipal solid waste. In general, the breakdown may occur naturally (e.g., in a landfill), or in an engineered environment (e.g., an anaerobic digester).

The term "biogas", as used herein, encompasses raw biogas and partially purified biogas, but does not encompass RNG, unless specified otherwise. Raw biogas refers to biogas collected at its source (e.g., a landfill or anaerobic digester). Raw biogas, which is largely composed of methane ($CH_4$) and carbon dioxide ($CO_2$), may also contain hydrogen sulfide ($H_2S$), water ($H_2O$), nitrogen ($N_2$), ammonia ($NH_3$), hydrogen ($H_2$), carbon monoxide (CO), oxygen ($O_2$), siloxanes, volatile organic compounds (VOCs), and/or particulates. For example, without being limiting, raw biogas typically has a $CH_4$ content between about 35% and 75% (e.g., average of about 60%) and a $CO_2$ content between about 15% and 65% (e.g., average of about 35%).

In general, the composition of raw biogas may depend on its source. For example, biogas produced from the AD of agricultural waste may have a higher methane content than biogas produced from a landfill (e.g., about 50-75%, compared to about 25-65%). In addition, biogas produced in a landfill may have a higher $N_2$ and $O_2$ content than biogas produced from the AD of agricultural waste. For example, the $N_2$ content of landfill biogas may be between 0% and 20%, compared to between 0% and 1% for digester biogas. In one embodiment, the raw biogas has a methane content between about 25% and 75% and a carbon dioxide content between about 15% and 65%, and the carbon dioxide and methane make up at least 75% of the biogas by volume.

The percentages used to quantify gas composition and/or a specific gas content, as used herein, are expressed as mol %, unless otherwise specified.

In general, the biogas used to produce the fuel may be obtained from one or more sources. In one embodiment, the biogas is obtained from one or more landfill sites. In one embodiment, the biogas is obtained from one or more AD systems, where each AD system has one or more anaerobic digesters. In one embodiment, the biogas is obtained from one or more landfill sites and/or from one or more AD systems.

In one embodiment, wherein biogas is obtained from an AD system having one or more anaerobic digesters, the one or more anaerobic digesters may be single-stage or multi-stage digestion systems, and/or may be designed and/or operated in a number of configurations including batch or continuous, mesophilic or thermophilic temperature ranges, and low, medium, or high rates. In one embodiment, wherein the biogas is obtained from an AD system having a plurality of anaerobic digesters, the plurality of anaerobic digesters is connected in series and/or in parallel.

In one embodiment, wherein biogas is obtained from an AD facility having one or more anaerobic digesters, the feedstock for the one or more anaerobic digesters is a single feedstock (e.g., manure or an energy crop) or is a mixed feedstock (e.g., manure and an energy crop), and may be in liquid form, solid form, and/or gaseous form.

In one embodiment, at least once source of biogas is an AD facility, which includes one or more anaerobic digesters, located on or near a farm. In this embodiment, the anaerobic digesters may be fed manure and/or other farm waste. In one embodiment, at least once source of biogas is an AD facility that includes one or more anaerobic digesters located at or near a wastewater treatment plant (WWTP). In one embodiment, at least once source of biogas is an AD facility that includes one or more anaerobic digesters that produce biogas as part of a conventional or cellulosic ethanol production process.

In general, each of the one or more sources of biogas may produce biogas at any rate. For example, one source of biogas may be a landfill project that generates biogas at a rate between 3000 and 6000 SCFM (standard cubic feet per minute), whereas another source of biogas may be an AD facility that produces less than 1000 SCFM of biogas. In one embodiment, each of the one or more sources of biogas produces biogas at a rate below 6000 SCFM. In one embodiment, each of the one or more sources of biogas produces biogas at a rate between 100 and 3000 SCFM. In one embodiment, each of the one or more sources of biogas produces biogas at a rate between 1000 and 3000 SCFM. In one embodiment, each of the one or more sources of biogas produces biogas at a rate between 1500 and 3000 SCFM.

Partial Purification

In one embodiment, the raw biogas produced at one or more sources is subjected to a partial purification. The term "partial purification", as used herein, refers to a process wherein biogas is treated to remove one or more non-methane components (e.g., $CO_2$, $H_2S$, $H_2O$, $N_2$, $NH_3$, $H_2$, CO, $O_2$, VOCs, and/or siloxanes) to produce a partially purified biogas, where the partially purified biogas fails to qualify as RNG and/or requires further purification in order to reach the purity of RNG.

In one embodiment, the partial purification removes $H_2O$. Without being limiting, raw biogas may be fully saturated with water vapour and/or may have a water content of about 7% (at 40° C.). Removing $H_2O$ is advantageous since moisture can condense into water or ice when passing from high to low pressure systems, which may cause corrosion, may result in clogging, and/or may interfere with gas flow and pressure measurements (e.g., causing system control problems). In addition, the presence of water may cause hydrates to form. In one embodiment, the partial purification removes more than 90%, 92%, 94%, 96%, or 98% of the $H_2O$ present in the raw biogas. In one embodiment, the partial purification removes more than 99% of the $H_2O$ present in the raw biogas. In one embodiment, the partial purification removes sufficient $H_2O$ from the raw biogas that the $H_2O$ content of partially purified biogas more than meets the applicable $H_2O$ content specifications for RNG. In one embodiment, the partial purification does not remove $H_2O$. In one embodiment, the partial purification removes sufficient moisture to provide the partially purified biogas with a $H_2O$ concentration less than 0.4 g/m³ of biogas or less than 0.2 g/m³ of biogas. In one embodiment, the partial purification includes a $H_2O$ removal stage that uses refrigeration techniques or desiccant drying. In one embodiment, the partial purification includes multi-stages of $H_2O$ removal (e.g., first stage of $H_2O$ removal followed by a second stage of $H_2O$ removal), which may or may not be consecutive. In one embodiment, $H_2O$ is removed using a standard biogas dehumidifier.

In one embodiment, the partial purification removes $H_2S$. Without being limiting, raw biogas may have a $H_2S$ concentration between about 0 and about 6700 ppm(v) (e.g., 0-10,000 mg/m³). $H_2S$ is both poisonous and corrosive, and can damage piping, equipment, and instrumentation. $H_2S$ can be reactive with many metals, and the reactivity may be higher at higher concentration and pressure, and/or in the presence of water. In one embodiment, the partial purification removes more than 90%, 92%, 94%, 96%, or 98% of the $H_2S$ present in the raw biogas. In one embodiment, the partial purification removes more than 99% of the $H_2S$ present in the raw biogas. In one embodiment, the partial purification removes sufficient $H_2S$ from the raw biogas that the $H_2S$ content of partially purified biogas more than meets the applicable $H_2S$ content specifications for RNG. In one embodiment, the partial purification removes sufficient $H_2S$ from the raw biogas that the $H_2S$ content of partially purified biogas is safer to transport but requires additional $H_2S$ removal to meet RNG standards. In one embodiment, the partial purification 20 does not remove $H_2S$. In one embodiment, the partial purification removes sufficient $H_2S$ from the raw biogas that the $H_2S$ concentration of partially purified biogas is less than 200 ppm(v), 100 ppm(v), 50 ppm(v), 40 ppm(v), 30 ppm(v), 20 ppm(v), 10 ppm(v), or 6 ppm(v). In one embodiment, the partial purification includes a first stage of $H_2S$ removal (e.g., biological) followed by second stage of $H_2S$ removal (e.g., an adsorption bed), which may or may not be consecutive. In one embodiment, $H_2S$ is removed using a commercial $H_2S$ removal unit (e.g., based on activated carbon, molecular sieve, iron sponge, water scrubbing, NaOH washing, and/or biofilter or biotrickling filter technologies).

In one embodiment, the partial purification removes $CO_2$. Without being limiting, raw biogas may have a $CO_2$ content between about 15% and 65% (e.g., average of about 35%). Removing $CO_2$ may be advantageous if the $CO_2$ is not required for the fuel production process, because the $CO_2$ makes it more costly to compress and transport (e.g., relative to pipeline NG, per unit of energy delivered). Even removing half of the $CO_2$ present in raw biogas can significantly reduce the mass of gas that needs to be compressed and/or transported. For example, removing a significant quantity of $CO_2$ can decrease the number of trucks and/or runs required. In addition, the $CO_2$ in raw biogas may be associated with phase change issues when $CO_2$ is compressed or depressurized. In one embodiment, the partial purification removes more than 90%, 92%, 94%, 96%, or 98% of the $CO_2$ present in the raw biogas. In one embodiment, the partial purification removes more than 20%, 30%, 40% or 50% of the $CO_2$ present in the raw biogas. In one embodiment, the partial purification removes between about 5% and 20% of the $CO_2$ present in the raw biogas. In one embodiment, the partial purification removes less than 5% of the $CO_2$ present in the raw biogas. In one embodiment, the partial purification does not substantially remove $CO_2$. In one embodiment, the partial purification removes sufficient $CO_2$ from the raw biogas that the $CO_2$ content of partially purified biogas is less than 25%. In one embodiment, the partial purification removes sufficient $CO_2$ from the raw biogas that the $CO_2$ content of partially purified biogas is less than 20%, 15%, 10%, or 8%. In one embodiment, the partial purification removes sufficient $CO_2$ from the raw biogas that the $CO_2$ content of partially purified biogas is less than 5%. In one embodiment, the partial purification removes sufficient $CO_2$ from the raw biogas that the $CO_2$ content of partially purified biogas is less than 4%. In one embodiment, the $CO_2$ is removed by absorption (e.g., water scrubbing, organic physical scrubbing, chemical scrubbing), pressure swing adsorption (PSA), membrane permeation, and/or cryogenic upgrading.

Removing $CO_2$ from biogas is typically associated with biogas upgrading. The term "biogas upgrading", as used herein, refers to a process that increases the calorific value of biogas by removing at least $CO_2$ and/or $N_2$. In one embodiment, the partial purification includes a partial biogas upgrading. Optionally, biogas upgrading may also remove $H_2S$, $H_2O$, $N_2$, $NH_3$, $H_2$, CO, $O_2$, VOCs, siloxanes, and/or particulates. The removal of $H_2O$, $H_2S$, VOCs, siloxanes, and/or particulates from biogas may be referred to as biogas cleaning. In one embodiment, the partial purification removes sufficient $CO_2$ to increase the calorific value or heating value by at least 50 BTU/scf, at least 100 BTU/scf, at least 150 BTU/scf, at least 200 BTU/scf, or at least 250 BTU/scf. In one embodiment, the partial purification removes sufficient $CO_2$ to increase the heating value to at least 600 BTU/scf, at least 700 BTU/scf, or at least 800 BTU/scf, but retains sufficient $CO_2$ and/or $N_2$ such that the heating value does not exceed 900 BTU/scf, 925 BTU/scf, or 950 BTU/scf.

In one embodiment, the partial purification removes at least $H_2O$ and $H_2S$. In one embodiment, the partial purification removes significant amounts of $H_2O$ and $H_2S$ from the raw biogas, while a majority of the $CO_2$ remains. In general, it may be advantageous to remove $H_2O$ and/or $H_2S$ prior to transport to reduce corrosion and/or safety concerns.

In one embodiment, the partial purification removes a significant amount of $H_2O$, $H_2S$, and $CO_2$ from the raw biogas, but does not significantly reduce the amount of $N_2$. In this embodiment, contaminants such as $O_2$, $NH_3$, VOCs, siloxanes, and/or particulates are optionally removed during the partial purification.

In general, the partial purification may be achieved using a stationary or mobile purification system, or some combination thereof, based on any suitable method/technology, or combination of methods/technologies, in one or more stages, as known in the art. For example, while separate stages may be provided to remove each of the selected components, it may be advantageous to select technologies that simultaneously remove more than one component. For example, $H_2S$ may be removed during some $H_2O$ removal technologies. In any case, since the removal of one or more components during the partial purification does not need to be extensive, less costly equipment/technologies may be used. For example, in one embodiment, the partial purification includes $CO_2$ removal using a mobile membrane system. In this embodiment, the mobile membrane system may remove sufficient $CO_2$ from the biogas to improve compressibility of the biogas, but may require further $CO_2$ removal to qualify as RNG.

In one embodiment, the partial purification yields a partially purified biogas having a non-methane content that is at least 20%, at least 15%, at least 10%, or at least 8%. In one embodiment, the partially purified biogas has an inert content (e.g., $CO_2$ and/or $N_2$) that is greater than 10%. In one embodiment, the partially purified biogas has an inert content that is greater than 8%. In one embodiment, the partially purified biogas has an inert content that is greater than 5%. In one embodiment, the partially purified biogas has a methane content that is at least 60%, at least 70%, at least 80%, at least 85%, at least 90%, or at least 95%. In one embodiment, the partially purified biogas has a methane content that is at least 60% and a $N_2$ content that is at least 5%. In one embodiment, the partially purified biogas has a $CO_2$ content that is greater than 8%, greater than 10%, greater than 15%, greater than 20%, or greater than 25%.

Loading and Transport of Biogas

In general, the raw or partially purified biogas is fed into one or more pressure vessels. The term "pressure vessel," as used herein, refers to any container designed to hold fluid at a pressure greater than 14.7 psig (0.1 MPa) (e.g., a gas cylinder). In one embodiment, the biogas (i.e., raw or partially purified) is fed into the one or more pressure vessels as it is produced. In one embodiment, the biogas (i.e., raw or partially purified) is fed into the one or more pressure vessels from buffer storage. In one embodiment, the biogas (i.e., raw or partially purified) is fed into the one or more pressure vessels as it is produced and/or from buffer storage.

In one embodiment, the biogas (i.e., raw or partially purified) is fed into a single pressure vessel. In one embodiment, the biogas (i.e., raw or partially purified) is fed into a pressure vessel system that includes a plurality of pressure vessels that are connected by tubing, hose, and/or piping. In this embodiment, the pressure vessel system may also include a plurality of valves, where each valve controls flow to/from a particular pressure vessel and/or between two pressure vessels. In one embodiment, the pressure vessel system includes a plurality of gas cylinders securely assembled in a frame or container. The term "pressure vessel system", as used herein, refers to a single pressure vessel or a plurality of interconnected pressure vessels, and any associated piping, tubing, hoses, valves, etc., that can be filled from a single inlet (i.e., when appropriate valves are open).

In one embodiment, the pressure vessel system has a single inlet/outlet. In one embodiment, the pressure vessel system has multiple inlet/outlets (e.g., a separate inlet and outlet). In one embodiment, where the pressure vessel system includes a plurality of interconnected pressure vessels, the biogas (i.e., raw or partially purified) is fed into the pressure vessel system such that one pressure vessel is filled before another is filled. In one embodiment, where the pressure vessel system includes a plurality of interconnected pressure vessels, the biogas (i.e., raw or partially purified) is fed into the pressure vessel system such that multiple pressure vessels fill simultaneously. In one embodiment, where the pressure vessel system includes a plurality of interconnected pressure vessels, the biogas (i.e., raw or partially purified) is fed into the pressure vessel system such that all of the pressure vessels fill simultaneously.

In general, the pressure vessel system is movable from one location to another via some mode of transportation. For example, the pressure vessel system may be movable by vehicle (e.g., rail car, ship, or truck). The term "truck", as used herein, may refer to a straight truck, which may carry cargo in a body mounted to its chassis, or to a tractor-truck, which may carry cargo using a trailer (e.g., semi-trailer).

In one embodiment, the pressure vessel system is fixedly coupled to a vehicle. For example, in one embodiment, the pressure vessel system is mounted on a straight truck. In one embodiment, the pressure vessel system is detachably coupled to the vehicle.

In one embodiment, the pressure vessel system is mounted to and/or within a body configured to be detachably coupled to a vehicle. For example, in one embodiment, the pressure vessel system is mounted within a trailer that can be pulled by a tractor unit. In one embodiment, the pressure vessel system is mounted to or within a skid or shipping container configured to be loaded onto and off of a truck bed or trailer bed (e.g., by hook lift). In embodiment, the biogas is loaded into a pressure vessel system within in a trailer, where the pressure vessel system includes a plurality of pressure vessels mounted vertically or horizontally. In general, there may be any number of pressure vessels. In one embodiment, the number of pressure vessels is greater than 3. In one embodiment, the number of pressure vessels is between 1 and 10. In one embodiment, the number of pressure vessels is between 2 and 60.

In one embodiment, the biogas (i.e., raw or partially purified) is fed into a pressure vessel system that is decoupled from the vehicle. For example, in one embodiment, the biogas is fed into pressure vessel system mounted on a trailer or skid parked near a source of biogas, which can be coupled to a truck or tractor unit once the pressure vessel system is filled.

In general, the biogas (i.e., raw or partially purified) will be compressed as it fills the one or more pressure vessels (e.g., pressure vessel system). As a result, the pressure of the biogas in the pressure vessel will increase from a relatively low value (e.g., 2-3 psig or some heel pressure of the pressure vessel system) to a relatively high value (e.g. greater than 1000 psig) near the end of the filling process. As is known in the art, the increased pressure may be achieved using one or more compressors, each of which may be a multistage compressor. For simplicity, such compressor systems may be referred to simply as a "compressor." In one embodiment, the compressor includes a standard CNG compressor. In one embodiment, the compressor includes a 3-stage non-lubricated compressor.

In one embodiment, the biogas (i.e., raw or partially purified) is fed into one or more pressure vessels (e.g., pressure vessel system) until the pressure is greater than about 1000 psig (6.9 MPa), greater than about 1500 psig (10.3 MPa), greater than about 2000 psig (13.8 MPa), greater than about 2200 psig (15.2 MPa), greater than about 2400 psig (16.5 MPa), greater than about 2600 psig (17.9 MPa), greater than about 2800 psig (19.3 MPa), or greater than about 3000 psig (20.7 MPa). In embodiments where the pressure vessel system includes a plurality of pressure vessels, different pressure vessels may be at a substantially same pressure or different pressures. In one embodiment, all of the pressure vessels are at the same pressure (i.e., the operating pressure of the pressure vessel system).

In general, each pressure vessel may be constructed of any material and thickness suitable for holding biogas (i.e., raw or partially purified) at the maximum operating pressure (MOP). The MOP, which refers to the highest pressure expected during operation, is typically at least about 10% below the maximum allowable working pressure (MAWP). In one embodiment, the one or more pressure vessels are fabricated from carbon steel or stainless steel. In one embodiment, the one or more pressure vessels are fabricated from a composite material. The use of composite material may be advantageous in terms of reducing corrosion associated with $H_2O$ and/or $H_2S$, and/or in terms of transporting a greater mass of gas. In general, each pressure vessel, or the pressure vessel system, will have a pressure relief valve. A pressure relief valve is a safety device used to protect the pressure vessel or pressure vessel system from catastrophic failure. In general, the set pressure of the pressure relief valve will not exceed the MAWP.

In general, each pressure vessel may have a nominal pressure rating, which is reported for a certain temperature (e.g., ambient). For example, commercially marketed CNG cylinders often have a nominal pressure rating of 3000 psig at 70° F. (21° C.), 3600 psig at 70° F. (21° C.), or 5000 psig at 70° F. (21° C.). A pressure vessel may be designed to hold a pressure up to 1.25 times its nominal pressure rating. For example, a 3600 psig pressure vessel may be filled to 4,500 psig, or a 5000 psig pressure vessel filled to 6250 psig, before the pressure relief valve is activated. This safety factor reduces risks (e.g., venting gas) associated with temperature induced pressure increases. For example, if a pressure vessel filled with NG to 3600 psig at 70° F. was heated to 120° F., the pressure would significantly increase (e.g., to more than 4400 psig, depending on the composition of the NG). Since the temperature within a pressure vessel may increase as it is filled (e.g., due to the heat of compression), this safety factor may also facilitate the practice of filling a pressure vessel to a pressure higher than the nominal pressure rating so that once the contents cool (e.g., to ambient temperatures) the pressure is closer to the nominal pressure rating.

In one embodiment, each of the pressure vessels and/or the pressure vessel system has a nominal pressure rating that is greater than 1000 psig (6.9 MPa), greater than about 1500 psig (10.3 MPa), greater than about 2000 psig (13.8 MPa), greater than about 2200 psig (15.2 MPa), greater than about 2400 psig (16.5 MPa), greater than about 2600 psig (17.9 MPa), greater than about 2800 psig (19.3 MPa), or greater than about 3000 psig (20.7 MPa) (at 70° F.).

In one embodiment, the biogas (i.e., raw or partially purified) is fed into one or more pressure vessels (e.g., pressure vessel system) until the pressure is within about 1%, 5%, 10%, 15%, 20%, 25%, or 30% of the nominal pressure rating (i.e., but not exceeding the MAWP).

In one embodiment, the biogas (i.e., raw or partially purified) is fed into one or more pressure vessels (e.g., pressure vessel system) until the pressure (corrected for ambient temperature) is substantially the same as the nominal pressure rating. In one embodiment, the biogas (i.e., raw or partially purified) is fed into one or more pressure vessels until the pressure (corrected for ambient temperature) is within about 1%, 5%, 10%, 15%, 20%, 25%, or 30% of the nominal pressure rating (i.e., but does not exceed the nominal pressure rating).

The nominal pressure rating, in addition to the volume of the pressure vessel system, may determine the mass of biogas (i.e., raw or partially purified) that can be transported (i.e., per delivery). In one embodiment, the biogas (i.e., raw or partially purified) is fed into a pressure vessel system that has an internal volume of at least 5,000 L, at least 10,000 L, or at least 20,000 L (water volume). In one embodiment the pressure vessel system has an internal volume between about 10,000 L and about 100,000 L (water volume). In one embodiment, the pressure vessel system has an internal volume between about 20,000 L and about 60,000 L (water volume). In one embodiment, the pressure vessel system has an internal volume between about 30,000 L and about 40,000 L (water volume).

In addition, or alternatively, the mass of biogas (i.e., raw or partially purified) that can be transported per delivery may be limited by the total truck weight (truck plus payload). In one embodiment, the pressure vessel system can store at least about 5 tonnes of biogas, at least about 7.5 tonnes of biogas, at least about 10 tonnes of biogas, or at least about 12.5 tonnes of biogas. In one embodiment, the pressure vessel system can store between about 5 tonnes and about 15 tonnes of biogas. In one embodiment, the pressure vessel system stores between about 11 and about 13 tonnes of biogas (e.g., having a $CO_2$ content between about 20% and about 40%). In one embodiment, the gross weight of biogas and truck is about 80,000 lbs. In one embodiment the pressure vessel system can store at least 100,000 SCF, at least 150,000 SCF, at least 200,000 SCF, or least 400,000 SCF of CNG (at 59° F. and 3600 psig). In one embodiment the pressure vessel system can store between about 200,000 SCF and about 640,000 SCF of CNG (at 59° F. and 3600 psig). In one embodiment the pressure vessel system can store about 425,000 SCF of CNG (at 59° F. and 3600 psig).

In one embodiment, the biogas (i.e., raw or partially purified) is cooled as it is fed into one or more pressure vessels (e.g., pressure vessel system). In one embodiment, a cooler or heat exchanger is used to cool the biogas before and/or after the compression. In one embodiment, the biogas is cooled to less than 40° C. in order to increase the mass of biogas that can be transported. In one embodiment, the level of cooling is limited such that the temperature in the one or more pressure vessels is relatively high (e.g., relative to ambient). For example, in one embodiment, the level of cooling is selected such that the gas in the one or more pressure vessels (e.g., pressure vessel system) is transported at a temperature greater than 40° C., greater than 50° C., greater than 60° C., greater than 70°, or greater than 80° C. Transporting the gas at a relatively high temperature (e.g., 60° C.) advantageously may reduce the heat required during depressurization.

In one embodiment, the one or more pressure vessels (e.g., pressure vessel system), and/or the vehicle, includes a temperature controller (e.g., a cooler or heater) for adjusting the temperature of gas within the one or more pressure vessels. For example, in one embodiment, the one or more pressure vessels includes a heater (e.g., heating coil) disposed within and/or around the one or more pressure vessels.

In one embodiment, the one or more pressure vessels (e.g., pressure vessel system) are provided with an adaptive insulation system. In this embodiment, the one or more pressure vessels may be mounted on a body (e.g., trailer or shipping container) that includes one or more vents or panels that are switchable between open and closed modes of operation. For example, the vents may be actuatable louvers. In one embodiment, the body (e.g., trailer or shipping container) includes insulation on the exterior walls.

In one embodiment, the biogas (i.e., raw or partially purified) is fed into a pressure vessel system that is contained in a trailer or shipping container parked near a source of biogas. Without being limiting, when the pressure vessel system is relatively large (e.g., may contain more than 200,000 SCF of biogas at 59° F. and 3000 psig), it may take several hours to fill the pressure vessel system (e.g., between about 1 to 3 hours, or about 1.5 hours).

In one embodiment, the biogas (i.e., raw or partially purified) is fed into a plurality of pressure vessel systems, each contained in a separate trailer or shipping container parked near the source of biogas. In this embodiment, the biogas may be fed to different trailers one-at-a-time or in parallel (e.g., simultaneously). Feeding the biogas to a plurality of trailers is advantageous in that the fill rate may be lower. A lower fill rate may allow more time for the heat generated from the compression to dissipate and/or may increase the time between pick-ups.

Once the one or more pressure vessels are filled to the desired level, they may be transported. In one embodiment, the desired level is the maximum operating pressure. In one embodiment, the desired level is a pressure (corrected for ambient temperature) that is close to the nominal pressure rating. In one embodiment, the desired level is a predetermined weight. In one embodiment, the desired level is a predetermined density of the biogas.

Since the pressure of a gas is dependent on temperature, but the volume of the system remains constant, it may be advantageous to assess the fill level of each pressure vessel using density. In one embodiment, the extent to which a pressure vessel system is filled is assessed relative to a design density. The term "design density", as used herein with reference to a particular gas and pressure vessel system, refers the density of that gas if it were contained within the pressure vessel system at the nominal pressure/temperature rating of the pressure vessel system. If the density of a gas is greater than the design density, then the pressure vessel may be considered overfilled. If the density of the gas is much less than the design density, then the pressure vessel may be considered underfilled.

In one embodiment, the filled pressure vessel(s) are loaded or coupled to a vehicle for transportation. For example, if the filled vessel(s) are mounted on a trailer, the trailer may be coupled to the tractor unit. The vehicle may then haul the trailer (e.g., in a single or multiple configuration). The vehicle may be near the source of biogas during the filling process, or may arrive at a scheduled time or upon notification that the biogas is ready or almost ready for delivery.

In one embodiment, the vehicle is a dedicated vehicle that travels between the source of biogas and the destination (e.g., the fuel production facility). In one embodiment, one or more vehicles are provided to transport biogas from a plurality of biogas sources to the destination (e.g., a fuel production facility). In this embodiment, biogas from each biogas source is transported directly to the destination (e.g., in a hub and spoke configuration). Accordingly, the delivery system is more efficient. Moreover, it may facilitate receiving multiple biogas deliveries at the destination within a short time period (e.g., hours) such that the decanting of biogas from different deliveries may overlap and/or be contiguous.

In one embodiment, the vehicle alternates between picking up a filled trailer (i.e., a trailer containing one or more filled pressure vessels) from one of a plurality of biogas sources and delivering it directly to the destination, and picking up an empty trailer (i.e., a trailer containing one or more pressure vessels that are empty or at some heel pressure) and returning it to the same biogas source or another biogas source.

In one embodiment, the vehicle is one in a fleet of vehicles for delivering biogas (i.e., raw or partially purified) from a plurality of biogas sources to the destination. In one embodiment, the vehicle (or fleet of vehicles) is fueled by a biogas-derived fuel (e.g., a fuel containing biogas derived methane). Using biogas, partially purified biogas, bio-CNG, or bio-LNG may allow more biogas to be transported in jurisdictions that provide extra weight allowance for the same. In addition, it may lower the carbon intensity of the fuel produced at the fuel production facility.

Unloading the Biogas

Once the one or more pressure vessels (e.g., pressure vessel system) have been transported by a vehicle to the destination, the biogas (i.e., raw or partially purified) may be unloaded, and more specifically, may be decanted (removed) from the one or more pressure vessels (e.g., pressure vessel system).

In one embodiment, decanting the biogas (i.e., raw or partially purified) from the one or more pressure vessels (e.g., pressure vessel system) includes connecting the pressure vessel system to a pressure let down system.

In one embodiment, the destination is a receiving station that includes or can be connected to a pressure let down system. In one embodiment, the receiving station is close to or is at the fuel production facility. In one embodiment, the receiving station includes connecting means (e.g., high pressure piping, tubing, flexible hose, manifold, switching valves, couplings, etc.) for connecting to the pressure vessel system. In one embodiment, the receiving station includes a plurality of docks, each of which is designed to accommodate a different pressure vessel system. In one embodiment, the receiving station includes a plurality of docking stations, each of which can accommodate a trailer, skid, or shipping container.

In general, the pressure let down system may be any system that can reduce the pressure of the biogas to the desired level. For example, the pressure let down system may include one or more mechanical regulating devices (e.g., a pressure regulator or control valve) to reduce the pressure. In one embodiment, the pressure let down system includes a pressure regulator, a temperature and/or pressure sensor, one or more valves, a metering system, a control system, and/or temperature control (e.g., a heater). With regard to the latter, the expansion or throttling of a gas provided by a pressure regulator may result in Joule-Thomson cooling of the gas. In one embodiment, the pressure let down system includes a heater upstream and/or downstream of the pressure regulator. In one embodiment, the heater(s) is a commercially available gas line heater (e.g., for natural gas). In one embodiment, the heater(s) is a heat exchanger. In one embodiment, the heat supplied to the heat exchanger is supplied by fired natural gas, CNG, raw biogas, partially purified biogas, or RNG. In one embodiment, the heat supplied to the heat exchanger is supplied by a heated liquid bath, an electric heater, or a cross-exchange with a hot process. In one embodiment, the heater(s) is a catalytic heater, electric heater, hot water heater, hot oil heater, or glycol heater system. In one embodiment, the heat is waste heat from the fuel production process.

In one embodiment, the pressure let down system and/or receiving station includes a compressor for removing gas from the pressure vessel system at low pressures (e.g., scavenging compressor). In one embodiment, the pressure let down system and/or receiving station includes one or more venturi pumps. In one embodiment, the pressure let down system and/or receiving station includes a turboexpander. A turboexpander is a centrifugal or axial flow turbine through which a high pressure gas is expanded to produce work. The kinetic energy from the pressure letdown may be converted into useful mechanical energy, which may be used to drive a compressor or generator (e.g., for producing electricity or for direct drive of a compressor). In one embodiment, this energy is used at the receiving station (e.g., for compression) and/or for the fuel production process.

Figure 2A:
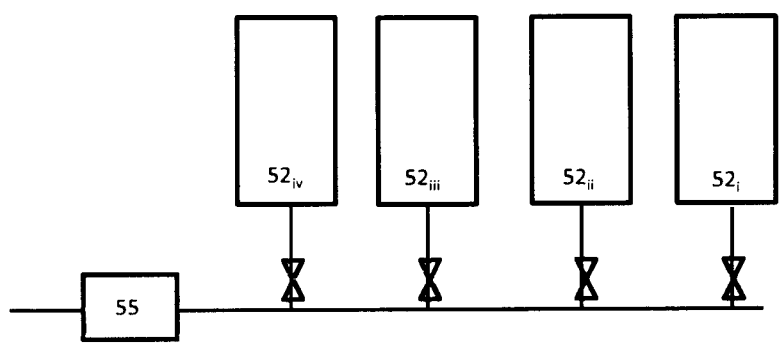
FIG. 2a is a schematic diagram illustrating a manifold, which may be used at the receiving station in accordance with one embodiment.
Figure 2B:
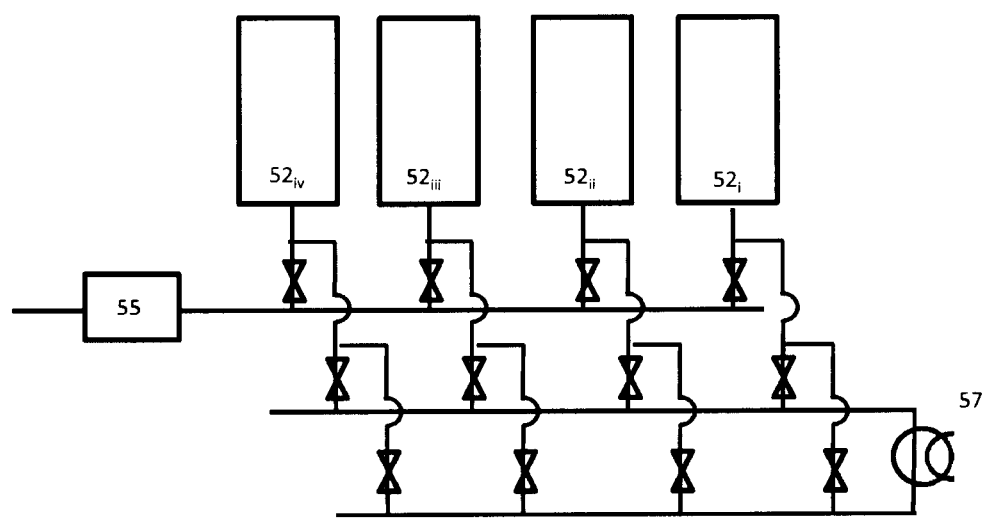
FIG. 2b is a schematic diagram illustrating another manifold, which may be used at the receiving station in accordance with one embodiment.
Figure 2C:
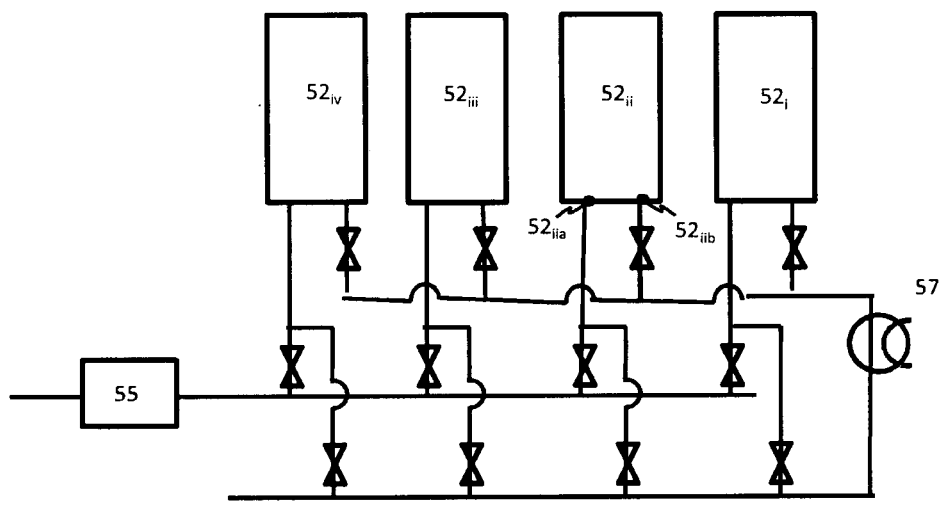
FIG. 2c is a schematic diagram illustrating yet another manifold, which may be used at the receiving station in accordance with one embodiment.

Referring to FIG. 1, there is shown an embodiment of a fuel production facility 50 in fluid communication with a receiving station 52. In this embodiment, the receiving station 52 includes a plurality of docking stations (e.g., $52_i$, $52_{ii}$, $52_{iii}$, $52_{iv}$). The plurality of docking stations is connected via a manifold that provides fluid communication with the fuel production facility 50. Some examples of different manifold configurations are illustrated in FIGS. 2a, 2b, and 2c, however, other configurations are possible as will be understood by those in the art. For illustrative purposes, a single pressure let down system 55 is shown, however, in some embodiments, more than one pressure let down system is provided. For example, in one embodiment, a pressure let down system is provided for each docking station. Optionally, the receiving station also includes at least one heater/heat exchanger 57 for heating gas in the manifold and/or within pressure vessels connected to the manifold. In one embodiment, the receiving station includes a plurality of heat exchangers. In one embodiment, the receiving station includes a heat exchanger for each docking station. In one embodiment, the receiving station includes a plurality of heat exchangers, where each heat exchanger is provided for a different receiving manifold. Referring again to FIG. 1, the fuel production facility 50 is illustrated as separate from the receiving station 52, however, in many embodiments, the receiving station 52 is part of the fuel production facility 50.

In general, depressurizing the pressure vessel system includes reducing the pressure of gas therein from a first pressure to a second pressure. In one embodiment, the first pressure is the pressure of the biogas just before the decanting process begins (e.g., the pressure of the biogas when it arrives at the receiving station), whereas the second pressure is the pressure of the biogas after the decanting process is complete (e.g., close to atmospheric pressure or some heel pressure). The term "heel pressure", as used herein, refers to the pressure of the gas remaining in the pressure vessel system after the decanting process is complete. For example, some pressure vessels having a bladder may require a heel pressure of about 200 psig (1.4 MPa).

In one embodiment, the depressurization reduces the pressure from an initial pressure that is greater than about 1000 psig (6.7 MPa), to a final pressure that is below about 500 psig (3.4 MPa), below about 400 psig (2.8 MPa), below about 300 psig (2.1 MPa), below about 200 psig (1.4 MPa), or below about 100 psig (0.7 MPa). In one embodiment, the depressurization reduces the pressure from an initial pressure that is greater than about 2000 psig (13.8 MPa), to a final pressure that is below about 500 psig (3.4 MPa), below about 400 psig (2.8 MPa), below about 300 psig (2.1 MPa), below about 200 psig (1.4 MPa), or below about 100 psig (0.7 MPa). In one embodiment, the depressurization reduces the pressure from an initial pressure that is greater than about 2500 psig (17.2 MPa), to a final pressure that is below about 500 psig (3.4 MPa), below about 400 psig (2.8 MPa), below about 300 psig (2.1 MPa), below about 200 psig (1.4 MPa), or below about 100 psig (0.7 MPa). In one embodiment, the one or more pressure vessels are depressurized to atmospheric pressure. In one embodiment, the one or more pressure vessels are depressurized to a final pressure between about 150 psig (1.0 MPa) and about 300 psig (2.1 MPa).

In one embodiment, the depressurization reduces the pressure from an initial pressure to a final pressure by removing at least 50%, at least 60%, at least 70%, at least 80%, at least 90%, or at least 95% of the biogas (by mass) initially present in the one or more pressure vessels.

In one embodiment, the temperature of the biogas (i.e., raw or partially purified) before depressurization is between about 0° C. and about 80° C. For example, the temperature of the biogas may reflect ambient temperatures (e.g., winter temperatures) and/or may be related to process conditions (e.g., heat added or heat generated during the filling process).

In embodiments where the receiving station includes a plurality docks, each of which is designed to accommodate a different delivery (e.g., trailer or shipping container), different deliveries may be decanted consecutively (e.g., one trailer may be emptied before another trailer is emptied) or may be decanted concurrently (e.g., the decanting processes for one trailer may overlap the decanting process for another trailer). In embodiments where the decanting process for multiple deliveries is concurrent, the different deliveries may be decanted simultaneously or in an alternating manner.

In one embodiment, the flow rate (e.g., mass or volume) of gas during the decanting process (i.e., the decanting flow rate) of a particular delivery will be substantially constant. In one embodiment, the flow rate during the decanting process of a particular delivery will vary. For example, in one embodiment, the decanting flow rate switches between high and low decanting flow rates for each delivery. In one embodiment, the flow rate during the decanting process decreases step-wise (e.g., over 2 to 5 steps). In one embodiment, the decanting flow rate reaches zero for one or more time periods during the decanting process of each delivery.

In one embodiment, multiple deliveries are decanted in a stepwise, alternating manner. For example, in one embodiment, the receiving station includes 3 docking stations, each for accommodating a different trailer. In this embodiment, the stepwise decanting process may include the following steps, as outline in Table 1.

TABLE 1

| Stepwise, alternating decanting scheme | | | |
| --- | --- | --- | --- |
| Step | Trailer 1 | Trailer 2 | Trailer 3 |
| 1 | Hook-up | | |
| 2 | Decant first half | Hook-up | |
| 3 | Rest or heat | Decant first half | Hook-up |
| 4 | Rest or heat | Rest or heat | Decant first half |
| 5 | Decant second half | Rest or heat | Rest or heat |
| 6 | Un-hook | Decant second half | Rest or heat |
| 7 | Hook-up | Un-hook | Decant second half |

In the embodiment illustrated in Table 1, the decanting flow rate for each trailer alternates between some high constant value and zero. When the decanting flow rate is about zero, the biogas in the trailer is able to rest or settle, during which time the temperature of the biogas may move closer to ambient temperature as a result of heat transfer from/through the pressure vessels walls. In one embodiment, the biogas in the pressure vessel system is actively heated during this rest stage. Advantageously, this scheme can provide a substantially constant flow rate of biogas to the fuel production process (e.g., the flow alternates between trailers in a continuous fashion). Similar schemes are envisioned where the number of docking stations increases and/or each trailer is decanted in a greater number of blocks.

In the embodiment illustrated in Table 1, trailer 1 is decanted in three stages. In the first stage, trailer 1 is depressurized to a selected point. When the pressure reaches the selected point, the decanting switches over to the second trailer, while trailer 1 enters a rest stage. At the end of the rest stage, trailer 1 is again decanted (i.e., the third stage). Although decanting a trailer in stages may interrupt the decanting process for that trailer, the process may be configured such that switching between stages results in no discernable interruption of biogas flow to the pressure let down system.

In the embodiment described with reference to Table 1, only one trailer is actively decanted at a time. In other embodiments, multiple trailers may be decanted simultaneously. In embodiments where multiple trailers are decanted simultaneously, they may be decanted into the same receiving manifold or different receiving manifolds. In such embodiments, the system may be configured such that the total flow rate from the multiple trailers is constant at all times. As a given pressure vessel system is depressurized, the depressurized biogas may be fed to the fuel production facility/process. While the depressurized biogas may be fed to the fuel production process either directly or indirectly (e.g., via buffer storage), one advantage of the processes described herein is that separate buffer storage at the destination may be avoided.

In general, the depressurized biogas (e.g., raw or partially purified) may be of a temperature and/or pressure suitable for downstream processing. For example, in one embodiment, the depressurized biogas is warmed to prevent freezing of downstream equipment. In one embodiment, the depressurized biogas is relatively cold (e.g., relative to ambient). For example, some downstream processing, such as membrane separations or cryogenic separations, can benefit from higher pressures and/or lower temperatures. In one embodiment, the depressurized biogas fed to the fuel production process is at pressure greater than 200 psig (1.4 MPa), greater than 500 psig (3.4 MPa), or greater than 750 psig (5.2 MPa). In one embodiment, the depressurized biogas fed to the fuel production process is at temperature below 20° C., below 10° C., below 0° C., or below −10° C.

In embodiments where the pressure vessel system is transported in a body (e.g., trailer, skid, or shipping container) that is detachable from the vehicle, it may be advantageous to detach and park the body. For example, in one embodiment, a filled trailer is detached from the tractor unit and parked at the destination for the decanting process (e.g., at a dock), while the tractor unit picks up an empty trailer for delivery to a biogas source (e.g., the same or different) where it can be exchanged for a filled trailer.

In one embodiment, biogas (i.e., raw or partially purified) from a plurality of biogas sources is aggregated, thereby improving consistency of the fuel production process by averaging out the $CO_2/CH_4$ ratios, flow rates, and/or other variables. In addition, it may dilute impurities, thereby improving the fuel production process. Collecting biogas from multiple sources is advantageous because some fuel production processes can benefit from economies of scale.

Advantageously, since the decanting process may include one or more active heating steps, such a process may be beneficial in winter conditions where the ambient temperature may be relatively low (e.g., −20° C.).

Producing a Fuel Using the Biogas

In one embodiment, the decanted biogas (i.e., raw or partially purified) is used to produce a fuel. In one embodiment, the decanted biogas (i.e., raw or partially purified) is used to produce a transportation fuel. In one embodiment, the decanted biogas (i.e., raw or partially purified) is used to produce a liquid transportation fuel. In one embodiment, a transportation fuel is produced from one or more components of the raw or partially purified biogas.

In one embodiment, the fuel is produced from the $CO_2$ in the biogas (i.e., raw or partially purified). In this embodiment, the feed for the fuel production process may be the raw biogas or the partially purified biogas (e.g., the fuel production process may remove any undesirable components). Alternatively, the feed may be a gas containing $CO_2$ removed from the biogas. For example, as is well known, ethanol may be produced by subjecting a gas stream containing $H_2$ and $CO_2$ and/or CO, to a gas fermentation using hydrogen oxidizing chemoautotrophs. For example, the microorganisms used may include any bacteria from a genus selected from *Acetogenium, Acetobacterium, Acetoanaerobium, Butyribacterium* and *Clostridium*. In one embodiment, the microorganism used to produce ethanol is *Clostridium ljungdahlii*. In one embodiment, the fuel is produced from the $CO_2$ in the biogas (i.e., raw or partially purified) using a gas fermentation, wherein an acetogen (e.g., anaerobes that use the acetyl CoA pathway) converts a gases containing $CO_2$ and $H_2$, and/or CO to ethanol.

In one embodiment, the fuel is produced using the $CH_4$ in the biogas (i.e., raw or partially purified). In this embodiment, the feed for the fuel production process may be the raw biogas or the partially purified biogas (e.g., the fuel production process may include biogas upgrading or cleaning). Alternatively, the feed for the fuel production process may be RNG. For example, in one embodiment, the biogas (i.e., raw or partially purified) is transported to a biogas upgrading facility, and the RNG produced at the biogas upgrading facility is delivered to the fuel production facility as a fungible batch using a NG distribution system. In this case, the RNG is fed into a NG distribution system, and NG withdrawn at another location is used to produce the transportation fuel. Since many NG distribution systems may recognize the transfer or allocation of the environmental attributes of RNG injected into the distribution system to NG withdrawn at a different location, the withdrawn NG can be considered RNG. Such transfer may be made on a displacement basis, where transactions within the distribution system involve a matching and balancing of inputs and outputs. Typically the direction of the physical flow of gas is not considered.

In one embodiment, the fuel is produced by transporting the biogas (i.e., raw or partially purified) to a fuel production facility. In one embodiment, the fuel production facility includes a biogas upgrading system. As is known in the art, a biogas upgrading system may include one or more units and/or stages for removing $CO_2$, $H_2O$, $H_2S$, $N_2$, $O_2$, $NH_3$, VOCs, siloxanes, and/or particulates from biogas. In general, a biogas upgrading system may use any combination of chemical and/or physical technologies known in the art for upgrading biogas. For example, $H_2O$ may be removed by cooling, compression, absorption, adsorption, and/or coalescing filtration. $H_2S$ may be removed by adsorption on activated carbon (e.g., impregnated activated carbon such as ZnO impregnated carbon), adsorption on molecular sieve, adsorption using iron oxides (e.g., iron oxide impregnated wood chips (iron sponge)), iron oxide pellets, or proprietary iron-oxide media), physical absorption (e.g., water scrubbing), chemical absorption (e.g., NaOH washing), and/or biofilters or biotrickling filters. Siloxanes may be removed by filtration (e.g., activated alumina, activated carbon, graphite filtration, or silica gels, which absorb siloxanes from biogas), by condensation or cryogenic techniques, using synthetic resins, using liquid absorbents (e.g., Selexol™), using membranes, and/or using biological processes. Particulates (e.g., dust and/or dirt) may be removed by mechanical filters, centrifugal separation, screens, etc. $N_2$ may be removed by pressure swing absorption (PSA), membranes, and/or cryogenic systems. $O_2$ may be removed by catalytic oxidation, membranes, or low pressure PSA. $CO_2$ may be removed by absorption (e.g., water scrubbing, organic physical scrubbing, chemical scrubbing), PSA, membrane permeation, and/or cryogenic upgrading. For example, in one embodiment, the biogas upgrading system includes a dehumidifier, a scrubber, a membrane unit, a solvent extraction unit, a pressure swing adsorption unit, and/or a cryogenic unit. In one embodiment, the fuel production facility alternatively, or additionally, includes a system for mixing the partially purified biogas and/or upgraded biogas with a higher energy gas (e.g., propane and/or natural gas withdrawn from a distribution system) in order to increase its heat content and meet pipeline standards.

In one embodiment, the biogas (i.e., raw or partially purified) is used to produce RNG for use as a transportation fuel. In this embodiment, the fuel production facility may be a biogas upgrading facility. For purposes herein, the term "renewable natural gas" or "RNG" refers to biogas that has been upgraded to meet or exceed applicable natural gas pipeline quality standards and/or specifications, meet or exceed applicable quality specifications for vehicle use (e.g., CNG specifications), and/or that qualifies as RNG under applicable regulations. Pipeline specifications include specifications required for the biogas for injection into a natural gas commercial distribution system. Pipeline standards or specifications may vary by region and/or country in terms of value and units. For example, pipeline standards may require RNG to have a $CO_2$ level that is less than about 2% and/or a $CH_4$ level that is greater than 95%. In addition, or alternatively, NG pipeline standards may refer to the quality of the gas expressed as a heating value (e.g., in British Thermal Units (BTU)/standard cubic foot). NG pipeline standards may require, for example, that the heating value of RNG be greater than about 950 BTU/scf, greater than about 960 BTU/scf, or greater than about 967 BTU/scf. In one embodiment, the biogas (i.e., raw or partially purified) is used to produce RNG having a heating value greater than 925 BTU/scf, greater than 950 BTU/scf, or greater than 967 BTU/scf.

In one embodiment, the biogas (i.e., raw or partially purified) is used to produce RNG, and the RNG is injected into a distribution system. The RNG is then withdrawn at another location from the distribution system (e.g., using the displacement principle) and used as a transportation fuel (i.e., the transportation fuel is RNG).

In one embodiment, the biogas (i.e., raw or partially purified) is used to produce RNG (e.g., liquefied RNG or bio-LNG). Since LNG may be produced by cryogenic techniques (e.g., may use a cryogenic nitrogen rejection unit (NRU)), it may be particularly advantageous to use the decanted biogas (e.g., raw or partially purified) in the bio-LNG process since it may already be at low temperatures, thereby reducing cooling costs.

In one embodiment, the biogas (i.e., raw or partially purified) is used to produce a transportation fuel other than RNG. Some examples of transportations fuels other than RNG that may be produced from biogas, include, but are not limited to, hydrogen, methanol, ethanol, butanol, gasoline, diesel, dimethyl ether (DME), and methyl tertiary butyl ether (MTBE). For example, in one embodiment, the fuel production facility is a gas-to-liquid (GTL) plant, where methane is converted to longer-chain hydrocarbons such as gasoline or diesel.

In one embodiment, the transportation fuel is produced based on a one-step conversion process (e.g., partial oxidation of biogas-derived methane to methanol).

In one embodiment, the transportation fuel is produced based on a multiple-step conversion process (e.g., using a syngas intermediate). Syngas, which is a gas mixture including CO and $H_2$, may be formed by subjecting $CH_4$ to methane reforming (e.g., steam methane reforming (SMR), autothermal reforming (ATR), dry reforming (DMR), or partial oxidation (POX)). In one embodiment, the transportation fuel is produced using a process that includes the steam reforming of a gas stream containing biogas-derived methane (e.g., a stream of raw biogas, a stream of partially purified biogas, or a stream of RNG). The terms "biogas-derived methane" and "methane derived from biogas", as used herein, refer to methane obtained from biogas and/or to methane withdrawn from a fungible distribution system into which methane obtained from biogas is injected, where the withdrawn methane is recognized as possessing the environmental attributes of the injected methane.

In one embodiment, the biogas (i.e., raw or partially purified) is used to produce $H_2$. In one embodiment, $H_2$ is produced by subjecting biogas-derived methane to a SMR reaction to produce syngas, which is subject to a water gas shift reaction (WGS) to increase the concentration of the $H_2$, followed by a pressure swing adsorption (PSA) stage to purify the $H_2$. The purified $H_2$ may be considered renewable $H_2$, and can be used directly as a fuel, or can be used to produce gasoline and diesel having renewable content (e.g., see U.S. Pat. No. 8,753,854).

In one embodiment, the biogas (i.e., raw or partially purified) is used to produce methanol. Methanol may be formed in a methane-to-methanol process. For example, in one embodiment, the methanol is produced from biogas-derived methane using Imperial Chemical Industries (ICI) low pressure methanol (LPM) process, Katalco low pressure methanol process, Lurgi low pressure methanol process, Haldor-Topsoe process, or liquid process such as the liquid-phase methanol synthesis process (LPMeOH). Suitable catalysis may include copper, zinc, oxide, alumina, chromium oxide, or combinations thereof. The methanol may be used as a transportation fuel, or may be used to produce a transportation fuel (e.g., DME, methyl tertiary butyl ether (MTBE), biodiesel, or gasoline (e.g., in a methanol-to-gasoline (MTG) process)).

In one embodiment, the biogas (i.e., raw or partially purified) is used to produce ethanol. In one embodiment, the ethanol is produced by the gas fermentation of one or more components of the biogas. In one embodiment, the ethanol is produced by the gas fermentation of a gas stream comprising one or more components from syngas produced by methane reforming of the biogas (i.e., raw or partially purified). For example, the production of ethanol by the gas fermentation of syngas with anaerobic microorganisms is well known (e.g., see U.S. Pat. No. 10,202,622).

In one embodiment, the biogas (i.e., raw or partially purified) is used to produce gasoline. Gasoline may be produced by converting syngas to methanol, which is transformed into gasoline (e.g., a methanol-to-gasoline (MTG) process). In one embodiment, the fuel production process produces gasoline from biogas-derived syngas.

In one embodiment, the biogas (i.e., raw or partially purified) is used to produce diesel. Diesel may be produced using a gas-to-liquid (GTL) refinery process where methane is converted to longer-chain hydrocarbons via a syngas intermediate. For example, diesel may be produced using a Fisher-Tropsch type process. In one embodiment, the fuel production process produces diesel from biogas-derived syngas.

In one embodiment, the biogas (i.e., raw or partially purified) is used to produce DME. DME may be produced by catalytic dehydration of methanol. DME may be used as a fuel for diesel engines (e.g., a clean diesel alternative). In one embodiment, the fuel production process produces DME from biogas-derived methanol.

In each of the above described embodiments, where the feed to the fuel production process includes biogas-derived methane, the feed may be entirely derived from biogas (e.g., producing only renewable fuel) or may include a combination of fossil based methane and biogas-derived methane. For example, in one embodiment, the fuel production facility uses both NG and RNG as feedstocks (e.g., a blend).

Advantageously, using biogas-derived methane in the production of a transportation fuel can provide a fuel that is a renewable fuel and/or has renewable content. In embodiments where the feedstock for the fuel production includes a combination of fossil methane and biogas-derived methane, the portion of the fuel that is considered to be renewable and/or to have the renewable content, may be calculated (e.g., energy balance, or mass balance calculation). For example, in one embodiment, the biogas-derived methane is fed into a pipeline containing fossil methane, where the pipeline is used to feed the fuel production process. In one embodiment, the environmental attributes of the biogas-derived methane are transferred to the renewable fuel.

In one embodiment, a fuel credit or renewable energy credit associated with the biogas and/or transportation fuel is generated or caused to be generated. The term "cause" or "causing", as used herein, refers to arranging or bringing about a specific result (e.g., a withdrawal of a gas from a distribution system), either directly or indirectly, or playing a role in a series of activities through commercial arrangements such as a written agreement, verbal agreement, or contract.

The term "credit", "renewable fuel credit", or "fuel credit", as used herein, refers to any rights, credits, revenues, offsets, greenhouse gas rights, or similar rights related to carbon credits, rights to any greenhouse gas emission reductions, carbon-related credits or equivalent arising from emission reduction trading or any quantifiable benefits (including recognition, award or allocation of credits, allowances, permits or other tangible rights), whether created from or through a governmental authority, a private contract, or otherwise. The renewable fuel credit may be a certificate, record, serial number or guarantee, in any form, including electronic, which evidences production of a quantity of fuel meeting certain life cycle GHG emission reductions relative to a baseline (e.g., a gasoline baseline) set by a government authority.

The generation of fuel credits or renewable energy credit associated with the biogas and/or transportation fuel may be related to the corresponding life cycle GHG emission emissions. To determine life cycle GHG emissions associated with a transportation fuel, an analysis may be conducted to calculate the GHG emissions related to the production and use of the transportation fuel throughout its life cycle. Life cycle GHG emissions include the aggregate quantity of GHG emissions related to the full life cycle of the fuel, including all stages of fuel and feedstock production and distribution, from feedstock generation or extraction, through the distribution and delivery, and use of the finished fuel to the ultimate consumer. GHG emissions typically account for total net GHG emissions, both direct and indirect, associated with feedstock production and distribution, the fuel production, and distribution and use. As well be understood by those skilled in the art, the methodology used to determine the life cycle GHG emissions is typically dependent on applicable regulations (e.g., under which the fuel credit is generated).

In one embodiment, the fuel produced is a transportation fuel, and a fuel credit is generated or is caused to be generated. Fuel credits, such as Renewable Identification Numbers (RINs) under the US Environmental Protection Agency (EPA) Renewable Fuel Standard, or carbon credits under state supported low carbon fuel standards, can be lucrative.

In one embodiment, the transportation fuel has life cycle GHG emissions that are at least 20% less than the life cycle GHG emissions of a gasoline baseline using EPA methodology, preferably at least 50% or 60% less.

Increasing the Mass of Biogas Transported

In accordance with one embodiment, the process of producing a fuel from biogas (i.e., raw or partially purified) is improved by transporting biogas in one or more pressure vessels (e.g., pressure vessel system) such that the mass of biogas of a given composition transported per delivery (e.g., per trailer, skid, or shipping container) is increased.

In one embodiment, the mass of biogas (i.e., raw or partially purified) that is transported per delivery is increased by using pressures greater than 1000 psig (6.9 MPa) and/or transporting the biogas at a higher density than pipeline quality NG is typically transported.

The density of biogas and/or NG may depend on its composition. The estimated densities for biogas having a $CH_4$ content of 50%, a $CO_2$ content of 38%, a $N_2$ content of 10%, and an $O_2$ content of 2% and for NG having a $CH_4$ content of 97% a $CO_2$ content of 2%, and a $N_2$ content of 1%, at different temperatures, are shown in Table 2. The densities were calculated using the Peng Robinson Equation of State.

TABLE 2

Estimated density of biogas relative to NG

| Pressure (at 21° C.) | Density (kg/m³) | |
|---|---|---|
| | NG | Biogas |
| 1450 psig (10 MPa) | 84.4 | 158.1 |
| 2175 psig (15 MPa) | 131.1 | 256.2 |
| 2900 psig (20 MPa) | 173.0 | 339.1 |
| 3626 psig (25 MPa) | 207.9 | 400.1 |
| 4350 psig (30 MPa) | 236.5 | 450.5 |
| 5076 psig (35 MPa) | 260.3 | 489.3 |

Assessing the extent to which a pressure vessel is filled using density may be advantageous because it is independent of temperature. In contrast, assessing the extent to which a pressure vessel is filled using pressure may require temperature correction. In addition, assessing the extent to which a pressure vessel is filled using density is tied to the idea that the total truck weight may not exceed a predetermined maximum weight (e.g., due to transport regulations).

Truck/trailer systems for transporting CNG may be designed such that when filled with NG to the nominal pressure rating (at ambient temperature), the truck/trailer does not exceed a predetermined maximum weight limit (e.g., determined by transport or road regulations). If such truck/trailer systems are instead filled with biogas (i.e., raw or partially purified), which may be relatively heavy, then the weight of the truck/trailer may reach the predetermined maximum weight limit before the nominal pressure rating of the pressure vessels is reached. For example, referring again to Table 2, the density of biogas at 3626 psig (25 MPa) may be almost twice that for NG.

In accordance with one embodiment, the mass of biogas (i.e., raw or partially purified) that is transported per delivery is increased by transporting the biogas at a higher density than pipeline quality NG is typically transported. In one embodiment, a pressure vessel capable of transporting NG is filled with biogas and transported at a density that is greater than the design density of NG for that pressure vessel. The term "design density of natural gas" or "design density of NG", as used herein with reference to a specific pressure vessel system, refers to the density of NG having a $CH_4$ content of 97%, a $CO_2$ content of 2%, and a $N_2$ content of 1%, if the NG was at a pressure and temperature corresponding to the nominal pressure/temperature rating of the pressure vessel system. In one embodiment, a pressure vessel capable of transporting NG is filled with biogas and transported at a density that is about 1.1, 1.2, 1.3, 1.4, or 1.5 times greater than the design density of NG for that pressure vessel. According to one embodiment, the biogas is transported at about its design density. According to one embodiment, biogas is transported at a density that is about 0.3, 0.2, or 0.1 times less than the design density of the biogas (i.e., for that pressure vessel).

In one embodiment, the biogas is transported at a density greater than 190 kg/m$^3$, greater than 200 kg/m$^3$, greater than 210 kg/m$^3$, or greater than 220 kg/m$^3$. In one embodiment, the biogas is transported at a density greater than 250 kg/m$^3$, greater than 275 kg/m$^3$, greater than 300 kg/m$^3$, or greater than 325 kg/m$^3$. In one embodiment, the biogas is transported in a pressure vessel having a nominal pressure rating lower than 2175 psig at 70° F., at a density greater than 140 kg/m$^3$. In one embodiment, the biogas is transported in a pressure vessel having a nominal pressure rating lower than 2900 psig at 70° F., at a density greater than 180 kg/m$^3$. In one embodiment, the biogas is transported in a pressure vessel having a nominal pressure rating lower than 3626 psig at 70° F., at a density greater than 210 kg/m$^3$, greater than 220 kg/m$^3$, greater than 240 kg/m$^3$, or greater than 250 kg/m$^3$.

In one embodiment, the biogas (i.e., raw or partially purified) is delivered in a pressure vessel system (e.g., in a trailer), where the pressure vessel system includes a plurality of gas cylinders connected by tubing, and where each gas cylinder has a nominal pressure rating. In one embodiment, each of the cylinders is filled with the biogas to within 10%, 15%, or 20% of nominal pressure rating and/or such that the density of the biogas is greater than the design density of NG. In one embodiment, each of the cylinders is filled with biogas to a pressure that is at least 70%, 75%, 80%, 85%, 90%, or 95% of the nominal pressure rating. In one embodiment, each of the cylinders is filled with biogas to a density that is at least 10%, 15%, 20%, at least 25%, or at least 30% higher than the design density of NG (e.g., for the rating of those cylinders). In one embodiment, each of the cylinders is filled with the biogas to a pressure that is less than the corresponding maximum allowable working pressure (MAWP) and greater than 65%, 70%, or 75% of the maximum allowable working pressure.

In general, for a given gas cylinder, the mass of biogas that can be transported in that cylinder may be increased by filling the gas cylinder with as much biogas as possible within some safety margin (e.g., to a temperature corrected pressure close to the nominal pressure rating). However, as a result of transport weight limitations, this does not necessarily increase the mass of biogas transported when transporting a larger number of cylinders and/or a larger container volume. For example, consider filling a CNG trailer having a nominal pressure rating of 3600 psig at 70° F. with partially purified biogas having a density at 3600 psig at 70° F. that is higher than an average density of natural gas at 3600 psig at 70° F. As the biogas fills the CNG trailer, since the biogas is relatively heavy, the total truck weight (e.g., truck plus payload) may exceed transport weight limitations before the pressure reaches the nominal pressure rating. In accordance with one embodiment, the mass of biogas that is transported per delivery is increased by reducing the container volume (e.g., water volume) relative to that what would be used to transport NG at that nominal pressure rating. For example, in one embodiment, the container volume is reduced by reducing the number of gas cylinders.

While it may seem counterintuitive to decrease the number of cylinders when the goal is to increase the amount of gas transported, this approach has been found to increase the mass of biogas that can be transported. For example, consider the following example, where a trailer is designed to hold up to 40 gas cylinders, where each gas cylinder has a nominal pressure rating of 3600 psig (24.8 MPa) at 21° C., a water volume of about 1000 L, and an empty mass of about 400 kg (882 lbs). In this example, in order to comply with transport regulations, the total weight available for the gas cylinders and the gas should be below 26,000 kg (57,320 lbs). For the calculations, the temperature of the gas at the end of the loading process is assumed to be 50° C. and the pressure at 50° C. was assumed to be 4000 psig (which when temperature corrected, corresponds to a pressure of 3242 psig at 21° C.). At 50° C. and 4000 psig, NG may have a density of about 192.5 kg/m$^3$. Accordingly, the 40 cylinders of NG may weigh about 23,700 kg, and thus would not exceed the maximum weight limit (e.g., 26,000 kg).

Referring to Table 3, the same 40 cylinders could also be used to transport biogas containing 50% CH$_4$, 38% CO$_2$, 10% N$_2$, and 2% O$_2$. However, for biogas having this composition, the density at 4000 psig at 50° C. is 359 kg/m$^3$ such that the 40 cylinders of biogas would weigh about 30,360 kg, and thus would exceed the maximum weight limit (e.g., 26,000 kg). In order to stay below the maximum weight limit, the pressure at 50° C. could be reduced to about 2600 psig (or less). However, by removing 6 of the cylinders, and filling to a pressure of 4000 psig at 50° C., more biogas (i.e., a greater mass) may be transported (e.g., 12,206 kg compared to 9,812 kg).

TABLE 3

Mass of biogas transported

| | Number of cylinders | |
|---|---|---|
| | 40 | 34 |
| Mass of cylinders (kg) | 16,000 | 13,600 |
| Pressure of biogas at 50° C. (psig) | 2600 | 4000 |
| Density of biogas (kg/m$^3$) | 245.3 | 359 |
| Mass of biogas (kg) | 9,812 | 12,206 |
| Mass of gas cylinders and biogas (kg) | 25,812 | 25,806 |

In the above described embodiment, the mass of biogas that is transported per delivery is increased by reducing the container volume. Alternatively, the mass of biogas that is transported per delivery is increased by using a pressure vessel system having a lower nominal pressure rating than typically used for transporting CNG (e.g., less than 2900 psig or less than 3600 psig).

In the above-described example, a trailer is designed to hold up to 40 gas cylinders, where each cylinder has a nominal pressure rating of 3600 psig at 21° C., a water volume of about 1000 L, and an empty mass of about 400 kg (882 lbs). Referring to Tables 3 and 4, the pressure of the biogas was limited to about 2600 psig at 50° C. in order to avoid exceeding weight limitations. Now consider the case, also illustrated in Table 4, where the trailer contains 40 gas cylinders, where each cylinder has a water volume of 1000 L and a nominal pressure rating of 2400 psig at 21° C. As in the above-described example, the gas cylinders may be filled with biogas to a pressure of about 2600 psig at 50° C. However, since the gas cylinders have a much lower nominal pressure rating (e.g., 2400 psig compared to 3600 psig), the cylinders may be constructed with less material such that the mass of the cylinders is less than 16,000 kg. Accordingly, these cylinders may be filled to a higher density than the design density for NG, and thus carry more biogas (mass), without exceeding the maximum truck weight.

TABLE 4

Mass of biogas transported

|  | Number of cylinders | |
|---|---|---|
|  | 40 | 40 |
| Nominal pressure rating at 21° C. (psig) | 3600 | 2400 |
| MAWP (psig) | 4500 | 3000 |
| Mass of cylinders (kg) | 16,000 | <16,000 |
| Pressure of biogas at 50° C. (psig) | 2600 | 2600 |
| Density of biogas (kg/m³) | 245.3 | 245.3 |
| Mass of biogas (kg) | 9,812 | 9,812 |
| Mass of gas cylinders and biogas (kg) | 25,812 | <25,812 |

In one embodiment, where a plurality of cylinders are filled with biogas close to the nominal pressure rating and/or such that the density of the biogas is greater than the design density of NG, the mass of biogas that is transported per delivery is increased by using one or more pressure vessels having a nominal pressure rating that is less than 2500 psig (17.2 MPa), less than 2400 psig (16.5 MPa), less than 2200 psig (15.2 MPa), less than 2000 psig (13.8 MPa), less than 1800 psig (12.4 MPa), or less than 1600 psig (11.0 MPa). In one embodiment, each of one or more pressure vessels has a nominal pressure rating between about 1000 psig (6.9 MPa) and about 2000 psig (13.8 MPa). In this embodiment, the biogas may be filled close to the nominal pressure rating (e.g., within 15% of the nominal pressure rating).

In one embodiment, where a plurality of cylinders are filled with biogas (e.g., raw or partially purified), the mass of biogas that is transported per delivery is increased by filling the one or more pressure vessels to a pressure between 2000 psig (13.8 MPa) and 3000 psig (20.7 MPa), between 2200 psig (15.2 MPa) and 2800 psig (19.3 MPa), and between 2400 psig (16.5 MPa) and 2600 psig (17.9 MPa). Filling the one or more pressure vessels to a pressure above 2400 psig (16.5 MPa) (but below 3000 psig (20.1 MPa)) may be particularly advantageous in terms of balancing the mass of a certain composition of biogas that can be transported and the transportation costs. For example, at pressures below 2000 psig (13.8 MPa) a larger container volume, and thus additional trucks, may be required.

In one embodiment, the units of energy delivered per biogas delivery is increased by providing a partial purification prior to transportation that includes $CO_2$ removal (e.g. this increases the amount of methane transported). For example, in one embodiment, at least 10%, at least 20%, at least 30%, at least 50%, at least 60%, or at least 70% of the $CO_2$ in the raw biogas is removed. In this embodiment, the partially purified biogas may contain sufficient $CO_2$ that the density of the biogas is greater than the design density of NG.

Reducing Risk of Phase Change

In general, a gas whose pressure is reduced across a throttling valve may undergo a sudden temperature decrease as a result of the Joule-Thomson effect. Accordingly, pressure let down systems often include and/or may be used with one or more gas-line heaters (e.g., heat exchange systems) to prevent freezing of downstream sensitive instruments and pipelines. However, such gas-line heaters do not address the temperature drop of gas within the one or more pressure vessels being decanted (which also undergoes an expansion). A temperature drop within the one or more pressure vessels (e.g., pressure vessel system) is more likely when the gas is being unloaded. For example, when unloading a gas from a pressure vessel system it can be advantageous to provide a near-complete and rapid decanting of the gas from the pressure vessel system, so that the pressure vessel system may be transported for refilling. This may facilitate larger deliveries and/or reduce the number of trucks and drivers required, thereby reducing transportation related costs. However, since the gas is removed rapidly and to near completion during the unloading, there is less time for the gas to be heated by the pressure vessel walls.

A large temperature drop is generally expected within a pressure vessel when the depressurization is over a wide range of values (e.g., from over 3000 psig (20.1 MPa) down to below 500 psig (3.4 MPa)). For example, a pressure vessel containing CNG at about 3600 psig (24.8 MPa) may cool to −60° C. or −80° C. when depressurized to atmospheric pressure, or down to about −55° C. when depressurized down to 200 psig (1.4 MPa). For CNG, which is predominately methane (e.g., ~97%), the gas mixture inside the pressure vessel may remain a gas during the pressure drop. However, for a $CO_2/CH_4$ mixture having a significant $CO_2$ content, this temperature drop may be problematic. For example, if the temperature within the pressure vessel approaches the dew point of the mixture (e.g., at a specific temperature and pressure), some of the gas mixture may condense. Once liquid is formed, and the pressure continues to reduce, the liquid may boil, extracting significant heat from the pressure vessel. This may affect the mechanical properties (e.g., cause material fatigue), and thus may affect the maintenance and/or lifetime of the pressure vessel. In some cases, the temperature and/or pressure drop may cause solids (e.g., solid $CO_2$) to form, which may clog valves. In addition, or alternatively, a phase change may affect the composition of the biogas being decanted. Compositional changes may be particularly problematic if the decanted gas is fed directly for processing.

In accordance with one embodiment, the process of producing a fuel from biogas (i.e., raw or partially purified) is improved by reducing the risk of a phase change within the one or more pressure vessels (e.g., pressure vessel system) as the biogas is decanted. The temperature at which a gas mixture undergoes a phase change may be calculated and illustrated using a plot of phase boundaries by pressure versus temperature. In a multi-component system, the phase change between gas and liquid is typically illustrated using a bubble point curve and/or dew point curve (i.e., a dew line). A bubble point curve, which reflects pressure/temperature points at which the first bubble of vapor forms from a liquid phase system, separates the pure liquid phase from the multi-phase region (i.e., liquid and vapour). The dew line, which reflects pressure/temperature points at which the first liquid droplet is formed out of the gas phase, separates the pure gas phase from the multi-phase region (i.e., liquid and vapour). Dew lines for multi-component mixtures are well known in the art.

In one embodiment, the risk of a phase change is reduced by controlling the temperature and/or pressure within the one or more vessels to ensure that the temperature of biogas within the pressure vessel being decanted does not approach the boundary of the dew line for the gas mixture (e.g., with a 5° C. to 15° C. safety margin). In general, the dew line may be determined experimentally or calculated. In one embodiment, the risk of a phase change is reduced by controlling the temperature and/or pressure within the pressure vessel system during the decanting process such that, as the biogas is decanted, the temperature of the biogas remains at least 5° C. higher than an experimentally determined dew line. The dew line is measured by observing condensation of gas in a closed chamber. In one embodiment, the risk of a phase change is reduced by controlling the temperature and/or pressure within the pressure vessel system during the decanting process such that, as the biogas is decanted, the temperature of the biogas remains at least at least 5° C. higher than the calculated dew line. The term "calculated dew line", as used herein, refers to the dew line simulated for the Peng-Robinson Equation of State, and where the property parameters are taken from Aspen HYSYS V9. For example, in one embodiment, the temperature and/or pressure within the one or more pressure vessels is controlled by adjusting the rate of depressurization and/or by actively heating the gas within the pressure vessel system. In one embodiment, the risk of a phase change is reduced by controlling the temperature and/or pressure within the pressure vessel system during the decanting process such that, as the biogas is decanted, the temperature of the biogas remains at least at least 3° C. or 10° C. higher than a dew line of the biogas.

In one embodiment, the risk of a phase change is reduced by controlling the flow rate of gas removed from the one or more vessels (e.g., pressure vessel system). In general, when gas is shipped at high-pressure for off-loading at some destination, it may be advantageous to provide rapid decanting in order to improve efficiency of the delivery process. However, it has now been recognized that the delivery process may be improved for biogas by increasing the decanting time, while still keeping it below a certain limit. Slowing the rate of depressurization allows more time for the biogas to be heated (e.g., passively or actively), and thus may reduce the risk of phase changes. If the rate of depressurization is low enough, it may be possible to avoid the dew line with little to no active heating.

In one embodiment, the total decanting time is greater than 1 hour, greater than 1.5 hours, greater than 2 hours, greater than 2.5 hours, or greater than 3 hours. In one embodiment, the total decanting time is greater than 1 hour, greater than 1.5 hours, greater than 2 hours, greater than 2.5 hours, but less than 3 or 3.5 hours. For comparative purposes, a trailer containing 290,000 SCF of CNG may take less than one hour to decant when the decanting flow rate is about 5500 standard cubic foot per minute (SCFM). The term "total decanting time", as used herein, refers to the time elapsed from the beginning of the decanting process to the end of the decanting process for a particular delivery (e.g., trailer), and includes any time wherein the decanting flow rate is temporarily reduced (e.g., rest stages where the decanting flow rate is about zero) and/or when a warming gas is injected.

In one embodiment, the risk of a phase change is reduced by controlling a flow rate to provide a total active decanting time greater than 1 hour, greater than 1.5 hours, greater than 2 hours, greater than 2.5 hours, or greater than 3 hours. In one embodiment, the risk of a phase change is reduced by controlling a flow rate to provide a total active decanting time greater than 1 hour, greater than 1.5 hours, greater than 2 hours, greater than 2.5 hours, but less than 3 hours or 3.5 hours. The term "total active decanting time", as used herein, refers to the time (e.g., cumulative) that the decanting flow rate is greater than 0 SCFM for a particular delivery (e.g., trailer).

In general, the decanting flow rate may be substantially constant or may be varied during the decanting process (e.g., of a trailer). In one embodiment, the decanting flow rate, which is substantially constant, is less than 5000 SCFM, is less than 4000 SCFM, is less than 3000 SCFM, is less than 2000 SCFM, or is less than 1000 SCFM.

In one embodiment, the decanting flow rate is varied (e.g., continuously or step-wise). For example, in one embodiment, the decanting flow rate is relatively high at the beginning of the decanting process (e.g., above 5000 SCFM) and relatively low near the end of the decanting process (e.g., below 1500 SCFM).

In one embodiment, the decanting process includes one or more rest stages wherein the decanting flow rate is very small or negligible (e.g., 0 SCFM). In one embodiment, the decanting process for a delivery includes alternating the decanting flow rate between a high and low value. In one embodiment, the decanting process for a delivery includes using a high flow rate stage, followed by a medium flow rate stage, followed by a low flow rate stage. In one embodiment, the contents of the one or more pressure vessels are actively heated during the rest stage(s). In one embodiment, the contents of the one or more pressure vessels are not actively heated during the rest stage(s). In any case, one or more rest stages may increases the time that heat (e.g., from a heat exchanger or from ambient air) may pass through the pressure vessel walls and warm the biogas, and thus may avoid phase changes within the pressure vessel.

In one embodiment, the risk of a phase change is reduced by ensuring that the temperature of the biogas (i.e., raw or partially purified) is relatively high before the decanting process begins. For example, in one embodiment, the temperature of the biogas is greater than 40° C., greater than 50° C., greater than 60° C., greater than 70°, greater than 80° C., or greater than 90° C. In one embodiment, the temperature of the biogas is greater than 40° C. and less than 80° C. In general, the upper temperature range may be limited as a result of the capacity of the pressure vessel and/or to temperature ratings of the pressure vessel.

In one embodiment, the temperature of the biogas is relatively high because it was transported at an elevated temperature. For example, the biogas may be transported at an elevated temperature because of warm ambient temperatures and/or because it has retained some heat of compression generated during the loading process. For example, without being limiting, if the biogas is transported soon after the biogas loading process is completed, and if the travel time to the destination is less than 1 or 2 hours, the temperature of biogas to be decanted could be about 60° C.

In one embodiment, the temperature of the biogas (i.e., raw or partially purified) is relatively high because it is heated in the one or more pressure vessels. For example, in one embodiment, the biogas (i.e., raw or partially purified) is heated in the one or more pressure vessels before decanting, as part of the decanting process, or a combination thereof. In embodiments where the biogas is heated in the one or more pressure vessels as part of the decanting process, the biogas may be heated at a constant rate or variable rate. For example, in one embodiment, the biogas (i.e., raw or partially purified) is heated at particular times during the decanting process. In general, these may be short times (e.g., intermittent heating) or may be for longer blocks of time (e.g., for the latter half of the decanting process). In one embodiment, the biogas within the pressure vessel system is heated for at least one quarter of the total decant time.

As discussed above, gas-line heaters may be used with pressure let down systems in order to prevent freezing of downstream sensitive instruments and pipelines. In such cases, it may be advantageous to provide more heat at the beginning of the process when the pressure drop is the largest. In contrast, it has now been that found that when countering the cooling effects within the pressure vessels while decanting, it may be advantageous to provide more heat in the middle of the decanting process. In one embodiment, heating of the biogas in the one or more pressure vessels is initiated after the pressure of the biogas has been reduced by half.

Actively heating the biogas in the one or more pressure vessels allows the one or more pressure vessels to be depressurized in as short a time as possible without risking phase change within the gas mixture. In general, the biogas may be heated directly (e.g., within the vessel) or indirectly (e.g., through the walls of the vessel). For example, direct heating may be achieved by introducing a warming gas into the vessel, whereas indirect heating may be provided by heating wire wrapped around the pressure vessel.

In one embodiment, biogas in the one or more pressure vessels is heated indirectly through the walls of the pressure vessel(s). In general, the heat may be provided by any suitable heater (e.g., direct heater and/or heat exchanger). In one embodiment, the heat is waste heat generated during the fuel production process. In one embodiment, the heat is generated during the transportation process (e.g., engine heat).

In one embodiment, biogas in the one or more pressure vessels is heated by a heater (e.g., heat exchanger) that is in contact with the walls of the pressure vessel.

In one embodiment, biogas in the one or more pressure vessels is heated with warm air that fills an enclosed space containing the one or more pressure vessels (e.g., the inside of the trailer box or shipping container). In general, the warm air may be ambient air or may be generated by any suitable heater (e.g., the truck engine or another engine). In one embodiment, the warm air is circulated mechanically (e.g., using a fan). In one embodiment, the enclosed space includes an adaptive insulation system. For example, in one embodiment, the adaptive insulation system includes one or more panels or vents (e.g., louvers) that are actuatable between open and closed modes of operation. In one embodiment, when operated in the open mode of operation, the system promotes heat transfer between the one or more pressure vessels and the surrounding air, and when operated in the closed mode of operation is insulating. In one embodiment, the one or more pressure vessels are transported in a trailer or shipping container that includes insulation on the walls.

In one embodiment, the biogas in the one or more pressure vessels is heated directly by introducing a relatively warm gas (e.g., referred to as a warming gas) into the one or more pressure vessels during the decanting process. In one embodiment, the warming gas is introduced when the decanting process is in a rest stage (e.g., such that there is an alternating depressurization/repressurization of the pressure vessel system, with a net depressurization). In one embodiment, the warming gas is introduced into the pressure vessel system at the same time gas is being decanted (e.g., with a net depressurization). In any case, introducing the relatively warm gas into the pressure vessel system provides both heat and mass, and thus increases the enthalpy of the system. This can prevent a multi-phase system in both the pressure vessel system and the pressure let down system.

While it may seem counterintuitive to introduce gas into a pressure vessel system during the decanting process, particularly when the goal is to unload gas, it has been found that doing so may provide a faster decanting time (e.g., relative to an approach wherein the active decanting time is extended to allow heat transfer to the surroundings), and/or may be simpler and/or faster than heating the gas through the walls of the vessel. Moreover, it is compatible with the idea of adding heat when some of the gas has been already decanted.

In one embodiment, the warming gas is raw biogas, partially purified biogas, RNG, or NG. Using raw biogas, partially purified biogas, RNG, or NG may be advantageous in that no new components are mixed with the biogas being decanted.

In one embodiment, the warming gas is raw or partially purified biogas obtained from another delivery. In this case, the delivery providing the warming gas may be referred to as the supply tank and the pressure vessel system into which the warming gas is injected may be referred to as the receiving tank. In this embodiment, the warming gas from the supply tank may or may not be heated prior to being injected into the receiving tank. Sourcing the warming gas from a different delivery is particularly advantageous. For example, it can mix biogas from a plurality of biogas sources, which may dilute impurities and/or improve feed consistency. Moreover, since the supply tank may be at a higher pressure (e.g., at 3600 psig at 70° F.), while the receiving tank may be only partially full (e.g., at 1000 psig at 70° F.), the injection of the warming gas into the receiving tank may be pressure driven. In one embodiment, the selection of the supply and receiving tanks are selected to obviate the need for a compressor by providing a certain pressure differential. In one embodiment, the initial pressure differential is greater than 200 psig (1.4 MPa), is greater than 300 psig (2.1 MPa), is greater than 500 psig (3.4 MPa), is greater than 750 psig (5.2 MPa), is greater than 1000 psig (6.9 MPa), is greater than 1500 psig (10.3 MPa), or is greater than 2000 psig (13.8 MPa). Although introducing the warming gas into the receiving tank increases the aggregate quantity of gas that is removed from the receiving tank, it may reduce the time to remove all gas by avoiding phase changes.

In one embodiment, temperature of the warming gas is at least 20° C. warmer, at least at least 30° C. warmer, at least 40° C. warmer, or at least 50° C. warmer than the contents of the pressure vessel into which it is injected. In general, it may be advantageous for the warming gas to be at a temperature greater than about 15° C., greater than about 20° C., greater than about 25° C., greater than about 30° C., greater than about 40° C., greater than about 50° C., greater than about 60° C., greater than about 70° C., greater than about 80° C., greater than about 90° C., or greater than about 100° C. before being injected. In one embodiment, temperature of the warming gas is between about 30° C. and about 150° C. In one embodiment, temperature of the warming gas is between about 40° C. and about 80° C.

In one embodiment, the warming gas is obtained from a warm pressure vessel (e.g., which has been heated and/or arrives at the receiving station relatively warm). For example, if limited cooling is providing during compression of the biogas as it fills the one or more pressure vessels, the temperature of the delivery could be between 30° C. and 80° C. upon arrival at the receiving station.

In one embodiment, the warming gas is heated after leaving the supply tank and before being injected into the receiving tank. For example, in one embodiment, the warming gas is heated using a gas line heater to at least 30° C., at least 40° C., at least 50° C., at least 60° C., at least 70° C., at least 80° C., or at least 90° C. before being injected. In one embodiment, the warming gas is heated to about 80° C. In one embodiment, the warming gas is heated to between about 30 and 150° C. In one embodiment, the warming gas is heated to between about 30 and 100° C. In one embodiment, the warming gas is heated to between about 30 and 90° C. In one embodiment, biogas removed from one pressure vessel system is heated at a rate between about 200 to 1000 kW, between about 300 and 800 kW, or between about 350 and 700 kW. In one embodiment, the heat is added to the receiving tank at a rate of at least 250 to 400 kW.

In one embodiment, the warming gas introduced into a pressure vessel is produced by withdrawing a stream of biogas from the pressure vessel, heating it in a conduit (e.g., manifold) that loops back to the pressure vessel, and reintroducing it back into the pressure vessel, thereby increasing the temperature of biogas within the pressure vessel. In this embodiment, where the supply tank and the receiving tank are the same, the conduit and corresponding heater provide a heating loop. In one embodiment, biogas within a pressure vessel system is heated using a heating loop prior to being fed to the pressure let down system. In one embodiment, biogas within a pressure vessel system is heated using a heating loop during the decanting process (e.g., after some biogas has been decanted).

In one embodiment, the heater is a commercially available gas line heater (e.g., for natural gas). In one embodiment, the heater is a heat exchanger. In one embodiment, the heat supplied to the heat exchanger is supplied by fired natural gas, CNG, raw or partially purified biogas. In one embodiment, the heat supplied to the heat exchanger is supplied by a catalytic heater, electric heater, or a heated liquid bath (hot water or hot oil or glycol). In one embodiment, the heat supplied to the heat exchanger is provided by a cross-exchange with a hot process at the fuel production process.

In one embodiment, the warming gas is injected into the receiving tank in an amount selected to sufficiently adjust the temperature of biogas in the receiving tank. In one embodiment, the amount of warming gas introduced into the receiving tank is at least 10%, at least 20%, at least 30%, at least 40%, or at least 50%, w/w, of the gas present in the receiving tank.

In one embodiment, the warming gas is injected into the receiving tank at a specific time (or times) selected in dependence upon the measured pressure, temperature, and/or mass of biogas within the pressure vessel system. For example, in one embodiment, the warming gas is injected into the receiving tank at a pressure/temperature selected to avoid a phase change in the receiving tank. Such pressures/temperatures may, for example, be calculated and/or obtained from look-up tables. In one embodiment, the pressures/temperatures are calculated assuming an adiabatic, isentropic decompression. In one embodiment, the pressures/temperatures are calculated assuming a deviation from an adiabatic, isentropic decompression. For example, thermodynamic curves and/or the dew line can be calculated or simulated for a certain system (e.g., for a certain amount and/or composition of gas), as is known in the art. The injection of the warming gas may be timed to correspond to a pressure/temperature that prevents the system from approaching that dew point. For example, it has been calculated that a gas mixture containing about 50% $CH_4$, 38% $CO_2$, 10% $N_2$, and 2% $O_2$, and, weighing about 11.78 tonnes, at about 60° C., and pressurized to about 3000 psig (20.1 MPa), can be depressurized down to 920 psig (6.3 MPa) (−23° C.) without reaching the dew point (e.g., calculated to be −28° C.), assuming an adiabatic isentropic decompression. In this embodiment, it may be advantageous to introduce warming gas when the pressure reaches about 1000 psig (6.9 MPa). In general, the quantity of warming gas introduced, the rate at which it is introduced, and the timing over which it is introduced, may be selected to provide a large temperature jump, a gradual temperature increase, or to maintain the temperature at some value (e.g., +/−5° C.), for some time. In one embodiment, the temperature of the warming gas, the flow rate of the injected warming gas, and/or the injection duration is selected to avoid the dew line (e.g., +/−margin). In one embodiment, the temperature of the warming gas, the flow rate of the injected warming gas, and/or the injection duration is selected to cause the temperature/pressure of the system to skirt a portion of the dew line (e.g., +/−10° C.). In one embodiment, the temperature of the warming gas, the flow rate of the injected warming gas, and/or the injection duration is selected to cause the temperature of the biogas to be higher than −20° C. when the pressure is between 950 psig (6.6 MPa) and 1050 psig (7.2 MPa).

In one embodiment, the warming gas is introduced into the receiving tank when the pressure of the receiving tank is less than about 1500 psig (10.3 MPa), less than about 1000 psig (6.9 MPa), less than about 900 psig (6.2 MPa), or less than about 800 psig (5.5 MPa). In one embodiment, the warming gas is introduced into the receiving tank when the pressure of the receiving tank is between 500 psig (3.4 MPa) and 1500 psig (10.3 MPa), between 800 psig (5.5 MPa) and 1200 psig (8.3 MPa), or between about 900 psig (6.2 MPa) and 1100 psig (7.6 MPa). In one embodiment, the warming gas is introduced into the receiving tank in dependence upon an automated control system that uses monitored temperature and/or pressure (e.g., to avoid the phase change).

In one embodiment, the warming gas is injected into the receiving tank only once during the decanting process of a delivery (e.g., for one block of time, which could be at the beginning, middle, or end of the decanting process). In one embodiment, warming gas is injected into the receiving tank multiple times during the decanting process. In each case, the flow rate of the warming gas may be constant or may be varied. For example, in one embodiment, the warming gas is provided at a constant flow rate. In one embodiment, the warming gas is provided at a continuously increasing or decreasing flow rate.

In one embodiment, the pressure vessel system providing the warming gas and the pressure vessel system being decanted are connected to a manifold that can provide fluid communication between a plurality of pressure vessel systems (e.g., each corresponding to a different delivery), and that may provide isolation, pressure regulation, and/or directional flow control, between the different pressure vessel systems. For example, such a system may permit different approaches/strategies to selecting the pressure, and thus reduce operating costs. In addition, such a system may be configured to provide a constant flow of biogas to the fuel production facility.

In one embodiment, the pressure vessel system being decanted receives warming gas from a single supply tank. In one embodiment, the pressure vessel system being decanted receives warming gas from multiple supply tanks. For example, using warming gas from multiple supply tanks (e.g., deliveries), where each supply tank is at a different pressure, may facilitate using a scheme that relies on pressure driven gas transfer. In this embodiment, the supply tank may be selected in dependence upon its instant pressure and the instant pressure of the receiving tank.

Advantageously, introducing a rest stage, the use of a warming gas, and/or active heating within the decanting process may facilitate using faster decant flow rates while reducing the risk of phase changes during the decanting process. For example, consider the following comparative examples.

In Example A, a trailer containing 300,000 SCF of biogas is decanted at a constant decant rate of 5000 SCFM. In this case, the total decant time is 60 minutes, and the total active decant time is 60 minutes. If four trailers, each containing 300,000 SCF of biogas, are decanted sequentially, the total process takes 4 hours, with an average decanting time per trailer of 1 hour.

In Example B, a trailer containing 300,000 SCF of biogas is decanted at 7500 SCFM for 20 minutes, sits for 20 minutes where the decanting rate is about 0 SCFM, and then is decanted at 7500 SCFM for 20 minutes. In this case, the total decant time is 60 minutes, but the total active decant time is only 40 minutes. If multiple trailers containing 300,000 SCF of biogas are docked, then another trailer may be decanted during the rest stage of the $1^{st}$ trailer. Using this strategy, if four trailers, each containing 300,000 SCF of biogas, are decanted in this alternating pattern, the total process takes 160 minutes, with an average decanting time per trailer of 40 minutes. Accordingly, the process is more efficient and trailers may be swapped out more frequently. Moreover, it provides the decanted gas at a higher rate.

In Example B, the decanting process was divided into three equal time blocks. However, this alternating decanting/resting scheme may be used for any number of rest stages and/or for unequal time blocks. Advantageously, this alternating decanting/resting scheme may be particularly advantageous for biogas, for which the use of higher decanting flow rates may be otherwise not be possible due to risk of phase changes. For example, in one embodiment, the gas in the resting stage(s) is actively heated. In this embodiment, the relative timing and/or relative length of the rest stage(s) may be selected to avoid the dew line of the biogas (i.e., raw or partially purified).

Advantageously, avoiding the dew point may be achieved by actively heating the biogas in the middle and/or later stages of the decanting process (e.g., when there is less mass to heat). Accordingly, heating the gas mixture within the vessel can be more rapid and/or efficient. In one embodiment, the biogas in the one or more pressure vessels is heated after more than 20%, more than 30%, more than 40%, more than 50%, more than 60%, or more than 70% of the biogas (e.g., % by weight) has been decanted. Advantageously, heating the biogas within the one or more pressure vessels after some portion has been removed is compatible with heating the biogas by introducing a warming gas (i.e., since the pressure will be lower). In one embodiment, warming gas is introduced into the pressure vessel being decanted after more than 20%, more than 30%, more than 40%, more than 50%, more than 60%, or more than 70% of the biogas (e.g., % by weight) has been decanted. In this embodiment, the warming gas may be introduced during a rest stage or while the biogas is being decanted.

In general, heating the biogas during the decanting process may provide large and rapid temperature swings, may provide slow temperature changes, and/or may keep the temperature constant with time. For example, in embodiments where the biogas in the pressure vessel is actively heated by injecting a warming gas during rest periods, the temperature may swing between higher and lower values. In embodiments where the biogas is actively heated with a heat exchanger through the walls of the pressure vessel, or where the biogas is actively heated by simultaneously injecting a warming gas while the biogas is decanted, the temperature may vary slowly or may stay substantially constant. In one embodiment, the biogas (i.e., raw or partially purified) in the one or more pressure vessels is provided with sufficient heat to skirt the dew line (e.g., with some safety factor, e.g., 10° C.).

In one embodiment, the biogas (i.e., raw or partially purified) in the pressure vessel system is provided with sufficient heat to keep the temperature in the pressure vessel system above −25° C., above −20° C., above −15° C., or above −10° C. In this embodiment, the initial pressure may be above 2000 psig (13.8 MPa), above 2400 psig (16.5 MPa), above 2900 psig (20.0 MPa), or above 3600 psig (24.8 MPa). In one embodiment, the biogas is decanted from about 3600 psig (24.8 MPa) to 1200 psig (8.3 MPa), and the process includes avoiding the dew point by providing sufficient heat to keep the temperature within the pressure vessel system above −20° C. In one embodiment, the biogas is decanted from about 3600 psig (24.8 MPa) to 1200 psig (8.3 MPa), and the process includes avoiding the dew point by providing sufficient heat to keep the temperature within the pressure vessel system above −25° C.

In one embodiment, the biogas (i.e., raw or partially purified) in the pressure vessel system is provided with sufficient heat to keep the temperature in the pressure vessel system above −25° C., above −20° C., above −15° C., or above −10° C. when the pressure is between 1200 psig (8.3 MPa) and 800 psig (5.5 MPa). In one embodiment, the biogas (i.e., raw or partially purified) in the pressure vessel system is provided with sufficient heat to keep the temperature in the pressure vessel system above −25° C., above −20° C., above −15° C., or above −10° C. when the pressure is between 1100 psig (7.6 MPa) and 900 psig (6.2 MPa). In one embodiment, the biogas (i.e., raw or partially purified) in the pressure vessel system is provided with sufficient heat to keep the temperature in the pressure vessel system above −25° C., above −20° C., above −15° C., or above −10° C. when the pressure is 1000 psig (6.9 MPa).

In one embodiment, the biogas (i.e., raw or partially purified) is provided with at least 200 kW of heat. In one embodiment, the biogas (i.e., raw or partially purified) is provided with at least 300 kW, 400 kW, 500 kW, or 600 kW of heat. In one embodiment, the biogas (i.e., raw or partially purified) is provided with heat at a rate of between 200 to 1500 kW. In one embodiment, the biogas (i.e., raw or partially purified) is provided with heat at a rate of between 300 to 1000 kW. In one embodiment, the biogas (i.e., raw or partially purified) is provided with heat at a rate of between 250 to 400 kW. In one embodiment, the biogas (i.e., raw or partially purified) is provided with heat at a rate of between 400 to 600 kW.

In one embodiment, the heat is applied a rate of at least 300 kW for at least 10% of the decanting time, at least 20% of the decanting time, at least 30% of the decanting time, at least 40% of the decanting time, or at least 50% of the decanting time, for one delivery. In one embodiment, the heat is applied a rate of at least 300 kW for about 10 to 30% of the decanting time, for about 30 to 50% of the decanting time, for about 40 to 60% of the decanting time, or for about 50 to 70% of the decanting time.

In one embodiment, the decanting process includes decanting biogas contained in a first trailer, and using biogas from a second trailer as a warming gas to heat the biogas in the first trailer during the decanting process. In this embodiment, the first and second trailers are connected by piping, tubing, and/or hose (e.g., a manifold) that is coupled to a gas-line heater. In one embodiment, biogas decanted from the second trailer is heated by the gas-line heater at a rate of at least 300 kW before entering the first trailer as the warming gas.

In one embodiment, heating the biogas (i.e., raw or partially purified) in each delivery includes providing at least 200 kWh per delivery, at least 300 kWh per delivery, at least 400 kWh per delivery, or at least 500 kWh per delivery. In one embodiment, heating the biogas (i.e., raw or partially purified) in each delivery includes providing between 300 and 700 kWh per delivery, between about 400 and 650 kWh per delivery, or between about 450 and 600 kWh per delivery.

In one embodiment, heating the biogas (i.e., raw or partially purified) in each delivery includes providing at least 5 kWh per tonne of biogas, at least 10 kWh per tonne of biogas, at least 15 kWh per tonne of biogas, or at least 20 kWh per tonne of biogas. In one embodiment, heating the biogas (i.e., raw or partially purified) in each delivery includes providing between about 15 and 40 kWh per tonne of biogas, between about between about 15 and 35 kWh per tonne of biogas, or between about 15 and 30 kWh per tonne of biogas, over the decanting process.

In some of the above described embodiments the process of producing a fuel from biogas (i.e., raw or partially purified) is improved by reducing the risk of a phase change within the one or more pressure vessels by adding heat (e.g., actively or passively). In other embodiments, the temperature is controlled and/or risk of phase change is reduced by the decanting method and/or speed.

In one embodiment, the risk of phase change is reduced by withdrawing the biogas from the bottom of the one or more pressure vessels. In one embodiment, the risk of phase change is reduced by withdrawing the biogas from an orifice positioned in the bottom half of the pressure vessels. As biogas is decanted from a pressure vessel, the remaining biogas will cool as the pressure drops and the gas expands. This cooler (and heavier) gas may settle in the lower half of the pressure vessel. Withdrawing from the cooler region of the pressure vessel may increase the average temperature and thus may reduce the risk of phase change.

In one embodiment, the risk of phase change is reduced by withdrawing the biogas (i.e., raw or partially purified) from the bottom half of one or more pressure vessels, where the one or more pressure vessels includes a plurality of vertically oriented cylinders. Since an elongated cylinder oriented in an upright position may provide a higher temperature differential between the top and bottom of the pressure vessel, removing biogas from the bottom half of such a vessel may be more advantageous than other configurations.

In general, the biogas may be withdrawn from the bottom half of each pressure vessel using any suitable method. In one embodiment, the biogas (i.e., raw or partially purified) is withdrawn from the bottom half of the pressure vessel. In one embodiment, the biogas (i.e., raw or partially purified) is withdrawn from the bottom third of the pressure vessel. In one embodiment, the biogas (i.e., raw or partially purified) is withdrawn from the bottom quarter of the pressure vessel.

In one embodiment, the biogas (i.e., raw or partially purified) is withdrawn from a pressure vessel through an opening disposed in a bottom half of the pressure vessel, a bottom third of the vessel, or a bottom quarter of the vessel. In this embodiment, the opening may be in the wall of the pressure vessel or may be on a tube that extends into the pressure vessel (e.g. at the distal end of the tube). In one embodiment, the pressure vessel is a cylinder and the tube is co-axial with the cylinder. In one embodiment, the pressure vessel is a cylinder and at least the end of the tube is co-axial with the cylinder. In one embodiment, the tube has an orifice at a distal end of a tube, where the tube is substantially parallel to the longitudinal axis of the cylinder. In this embodiment, the biogas may be drawn in a direction parallel to the longitudinal axis of the cylinder, such that the colder gas at the bottom of the tank is removed before the warmer gas near the top and at the side of the tanks is removed. In one embodiment, the tube has one or more orifices on the sides of the tube. In one embodiment, the tube includes a plurality of orifices aligned in the longitudinal direction. For example, in one embodiment, the tube is provided with a first set of holes that extend in the longitudinal direction, along with a second set of holes also aligned in the longitudinal direction. In this embodiment. In this embodiment, the holes in the first and second sets may be aligned or be staggered, and may be side-by-side or may be disposed on opposing sides of the tube. Providing holes on the sides of the tube may be advantageous in terms of improving uniformity of the gas (e.g., composition and/or temperature).

Figure 3:
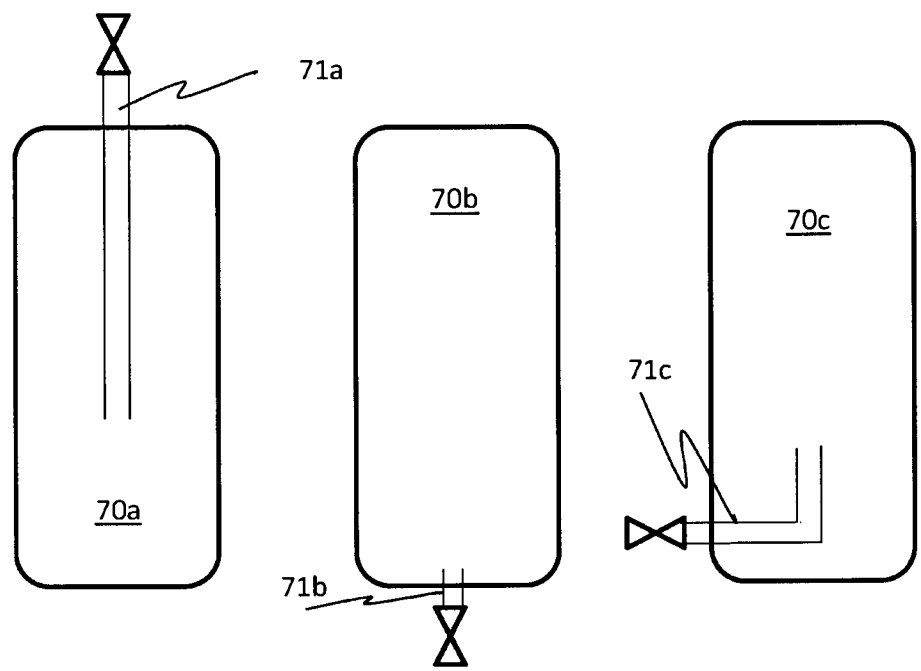
FIG. 3 is a schematic diagram illustrating different embodiments of pressure vessels for transporting biogas.

FIG. 3 illustrates various embodiments of a pressure vessel having a tube with an opening disposed in the bottom half. In these embodiments, the pressure vessel is a vertically oriented cylinder and the tube (71*a*, 71*b*, 71*c*), which is illustrated having an orifice at the distal end thereof, is the sole inlet/outlet to the corresponding pressure vessel (70*a*, 70*b*, 70*c*). For example, this tube may be used for injecting the biogas during the loading stage, withdrawing the biogas during the decanting stage, and/or for injecting a warming gas during the decanting process. In this embodiment, the distal end of the tube (and thus orifice) may be substantially centered (radially) within the cylinder. In one embodiment, the cylinder has an internal radius "R", and the orifice is at least ½×R away from the walls of the cylinder and/or from the bottom of the cylinder. Advantageously, this may facilitate removing the coldest gas first (i.e., the biogas near the walls and/or bottom may be warmer due to ambient heat transfer). In one embodiment, the orifice is disposed at least 0.3R away, at least 0.4R away, at least 0.5R away, at least 0.6R away, at least 0.7R away, or at least 0.8R away from an internal wall and/or bottom of the cylinder.

Figure 4:
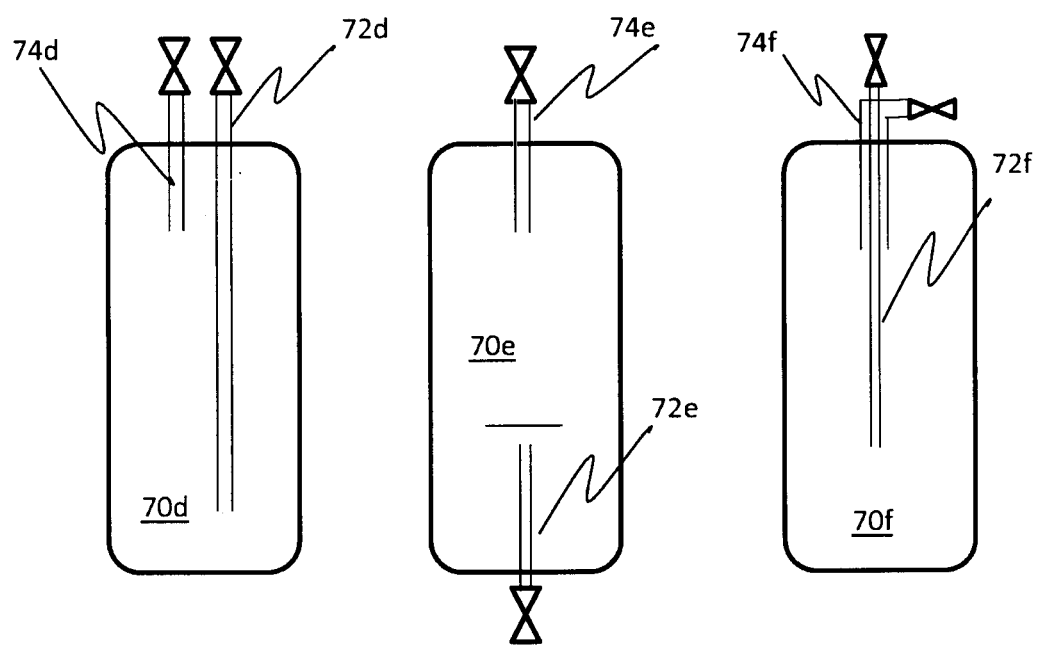
FIG. 4 is a schematic diagram illustrating other embodiments of pressure vessels for transporting biogas.
Figure 5A:
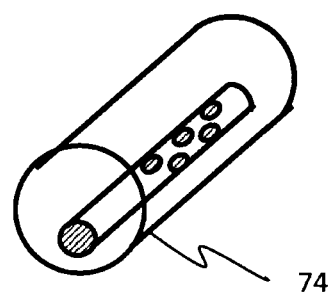
FIG. 5a is a schematic diagram illustrating an embodiment of a pressure vessel for transporting biogas in accordance with an embodiment of the invention.

In one embodiment, each pressure vessel in the pressure vessel system has a single inlet/outlet from which biogas is withdrawn/injected (e.g., see FIGS. 3 and 5*a*). In one embodiment, each pressure vessel has multiple inlet/outlets from which biogas may be withdrawn/injected. For example, FIG. 4 shows various embodiments where each pressure vessel (70*d*, 70*e*, 70*f*) includes two tubes, and where at least one of the tubes has an opening disposed in the bottom half of the pressure vessel. In these embodiments, each pressure vessel is a vertically oriented cylinder, and has tubes with lower distal ends (72*d*, 72*e*, 72*f*) and tubes with higher distal ends (74*d*, 74*e*, 74*f*). In pressure vessel 70*f*, the two tubes are co-axial, with a first tube 72*f*, nested within the second tube 74*f*. Optionally, each tube is provided with a diffuser or dissipater plate. Each of the tubes 72*d*, 72*e*, 72*f*, 74*d*, 74*e*, 74*f* may be used for injecting the biogas during the loading stage, withdrawing the biogas during the decanting stage, and/or for injecting a warming gas during the decanting process. Advantageously, the distal ends of tubes 74*d*, 74*e*, 74*f* are spatially separated from the distal ends of the tubes 72*d*, 72*e*, 74*f*, respectively. Accordingly, one may be used for decanting biogas while the other one is used for simultaneously injecting warming gas. For example, in one embodiment, the lower tubes 72*d*, 72*e*, 72*f* are used for withdrawing biogas during the decanting stage, while the higher tubes 74*d*, 74*e*, 74*f* are used for injecting warming gas. This embodiment has the advantage that the colder gas is removed first, and thus may help avoid phase changes in the biogas. In another embodiment, the higher tubes 74*d*, 74*e*, 74*f* are used for withdrawing biogas during the decanting stage, while the lower tubes 72*d*, 72*e*, 72*f* are used to inject warming gas. This embodiment may provide improved mixing/turbidity, and thus may reduce the risk of phase changes.

Figure 5B:
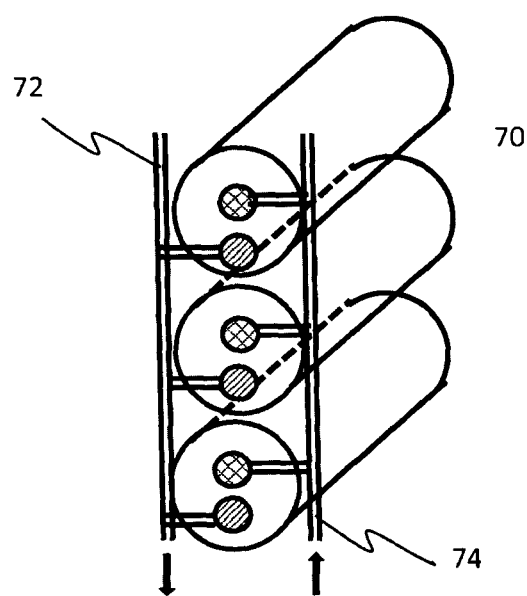
FIG. 5b is a schematic diagram illustrating an embodiment of a pressure vessel system for transporting biogas in accordance with an embodiment of the invention.

FIG. 5*a* shows an embodiment of a horizontally oriented pressure vessel having an inlet/outlet tube that extends into the pressure vessel and that has a plurality of orifices disposed thereon (e.g., disposed in the bottom half of the pressure vessel). FIG. 5*b* shows an embodiment of a pressure vessel system 70 comprising a plurality of horizontally oriented cylinders. In this embodiment, each cylinder has two inlet/outlets, one of which is configured to withdraw biogas during the decanting stage and one of which is configured to inject warming gas during the decanting stage. As shown in FIG. 5*b*, all of the inlets/outlets configured to withdraw biogas may be connected via a first manifold 72, while all of the outlets configured to inject warming gas may be connected via a second manifold 74. In one embodiment, a trailer containing this pressure vessel system 70 is docked at a receiving station (e.g., 52 illustrated in FIG. 1). In this embodiment, the first manifold 72 may be connected to a first inlet/outlet port $52_{iia}$, whereas the second manifold 74 may be connected to a second inlet/outlet port $52_{iib}$. Biogas withdrawn from the first manifold 72 is either directed to the pressure let down system 55 or to the heating system 57, whereas biogas from another delivery (e.g., stationed at docking port $52_i$) and heated by the heating system 57 is reinjected into the pressure vessel system 70 via manifold 74.

In one embodiment, the risk of phase change is reduced by decanting each pressure vessel system in more than one stage, wherein the pressure vessel system is heated in at least one stage, and/or wherein each stage is initiated by actuating valves that control the decanting of biogas from that pressure vessel system.

In one embodiment, the risk of phase change is reduced by disrupting the decanting of a pressure vessel system at some point during the unloading process. The term "disrupting", with respect to decanting (removing) biogas from a pressure vessel system, as used herein, refers to adjusting the flow rate (e.g., mass or volume) of gas leaving the pressure vessel system and/or introducing gas into the pressure vessel system during the decanting process. In one embodiment, the disruption is a pause in the decanting. In one embodiment, the disruption is a slowing of the decanting. In one embodiment, the disruption is initiated by introducing a warming gas into the pressure vessel system being decanted. In one embodiment, the disruption includes switching valves on a manifold to switch the decanting from one pressure vessel system to another pressure vessel system. In one embodiment, the disruption occurs at a point in the decanting process selected in dependence upon a pressure of the pressure vessel being decanted, a temperature within the pressure vessel being decanted, or a mass of the truck and payload. In one embodiment, the first disruption occurs when at least 25%, at least 30%, or at least 40% of the biogas has been decanted (e.g., by mass).

Conventionally, if a gas is transported in a pressure vessel system to another location for unloading, there will be no interruptions to the decanting process (e.g., the gas will be unloaded at a constant rate until all of the gas to be unloaded has been unloaded). However, it has now been found that disrupting the decanting can improve the unloading process. For example, as discussed above it may reduce the risk of phase changes within the pressure vessel system. In addition, it may facilitate providing the decanted biogas at different pressures.

DESCRIPTION OF SOME EMBODIMENTS

Figure 6:
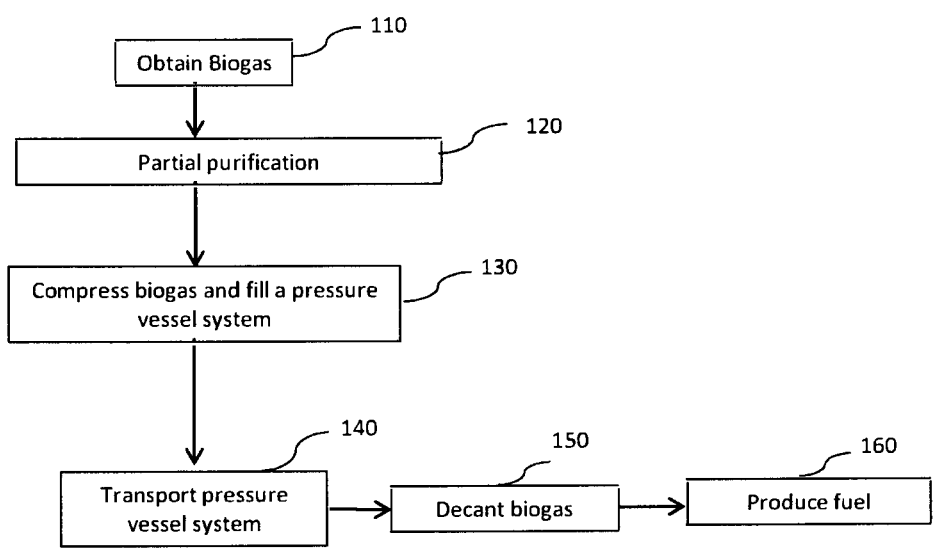
FIG. 6 is a flow diagram illustrating a method in accordance with an embodiment of the invention.

Referring to FIG. 6, there is shown a method in accordance with one embodiment of the instant invention. In step 110, raw biogas collected from a first biogas source. In step 120, the raw biogas is subjected to a partial purification process, including a drying and $H_2S$ removal process (if required). In step 130, the partially purified biogas is compressed and fed into a first pressure vessel system contained in a trailer. The pressure vessels system includes a plurality of gas cylinders (e.g., 35), each having a predetermined water volume (e.g., 1000 L), and in fluid communication with the other cylinders via tubing, piping, and/or hose. The pressure vessel system, which has a predetermined nominal pressure rating (e.g., 2000 psig (13.8 MPa) at 21° C.), is filled to a pressure (e.g., to 2200 psig (15.2 MPa)), which is higher than the nominal pressure rating due to the heat of compression (e.g., the temperature of the biogas is 50° C. at the end of the loading). Since the biogas has a significant $CO_2$ content, it is denser than the average density of pipeline quality natural gas at the same temperature and pressure. In step 140, the pressure vessel system containing the pressurized partially purified biogas is coupled to a truck, which transports the partially purified biogas to a receiving station located at or near the fuel production facility. By the time the truck and trailer reach the receiving station the temperature may have fallen (e.g., to about 40° C.).

In step 150, the pressure vessel system is connected to a receiving manifold at the receiving station, which includes multiple docks, each of which is configured to accommodate a different trailer. The pressurized partially purified biogas is then decanted. In one embodiment, the biogas in the pressure vessel system is heated with a warming gas. In embodiments where the pressure vessel system has a single inlet/outlet, this may include decanting in an alternating manner with biogas from another trailer. In embodiments where the pressure vessel system has an inlet and a separate outlet, this may include simultaneously injecting warming gas and decanting biogas from the same trailer. In this embodiment, the biogas in the pressure vessel system is decanted to a lower pressure corresponding to some heel pressure (e.g., 150 psig (1 MPa) or 200 psig (1.4 MPa)).

In step 160, the decanted biogas is fed into the fuel production facility and a fuel is produced. In one embodiment, the fuel production facility produces ethanol by the gas fermentation of syngas. The syngas is produced by steam methane reforming the decanted biogas (i.e., raw or partially purified). Alternatively, the decanted biogas (i.e., raw or partially purified) is upgraded (e.g., to RNG) or partially upgraded to remove some $CO_2$ before the steam methane reforming. In one embodiment, the $CO_2$ removed during the upgrading or partial upgrading is used to adjust the $H_2/CO_2/CO$ ratio of the syngas in order to optimize the gas fermentation.

Advantageously, since the fuel is produced from biogas (i.e., raw or partially purified) obtained from a plurality of biogas sources, the fuel production facility may be a relatively large-scale facility and may profit from the economies of scale. For example, conventionally, gas fermentation has been limited to feedstocks based on industrial wastes (e.g., steel mill). However, by implementing the improvements disclosed herein the economics for producing ethanol from biogas may be improved. Moreover, since the biogas is provided from a plurality of sources, there are significant improvements in terms of flow rate and/or consistency. For example, since the biogas production rate at each biogas source can be variable (e.g., may vary with time of year), collecting biogas from multiple sources can provide a relatively constant supply of biogas to the fuel production facility. Moreover, since the biogas from multiple sources may mix during or after the decanting process, the fuel may be produced from an aggregate of gases. Producing a fuel from an aggregate of gases is advantageous in that in may improve flow rates, dilute impurities, and/or otherwise average out variability.

Further advantageously, the fuel production process may benefit from the pressurization of biogas. In general, it is not common to pressurize biogas having a significant $CO_2$ content to pressures above 1000 psig (6.9 MPa)(e.g., for perceived challenges and/or economic reasons). However, since the biogas is transported at elevated pressures (e.g., greater than 1000 psig (6.9 MPa)), these elevated pressures may be used to improve the fuel production process. For example, if the fuel production process includes the step of subjecting the decanted raw or partially purified biogas to a process (e.g., methane reforming, $H_2S$, or $CO_2$ removal) that performs better at higher pressures, the decanting process may designed to provide the decanted biogas at this pressure (e.g., 600-1000 psig). For example, a trailer may be decanted to 1000 psig (6.9 MPa) in a first stage, and then to 200 psig (1.4 MPa) in a second stage. The biogas decanted in the first stage may be fed directly into the fuel production process at 1000 psig (6.9 MPa) as a feedstock, whereas the biogas decanted in the second stage is compressed to 1000 psig (6.9 MPa) or is used elsewhere in the process at a lower pressure (e.g., to alter $CO_2/CO$ ratios or as a fuel for producing heat/electricity for the process). This may reduce compression costs.

Further advantageously, since the decanting process may include one or more active heating steps, such a process may be beneficial in winter conditions where the ambient temperature may be relatively low (e.g., −20° C.).

Furthermore, since biogas is transported from a plurality of biogas sources directly to the receiving station (e.g., in a hub-and-spoke configuration), the receiving station may receive multiple overlapping deliveries. Accordingly, the unloading of different deliveries may overlap and/or be contiguous. More specifically, the flow of decanted biogas provided to the fuel production process may be essentially uninterrupted without having to use separate buffer storage. Avoiding buffer storage at the fuel production facility reduces costs.

The above-described fuel production process may make the production of a transportation fuel from biogas economically feasible and may open up additional options for small biogas plants (e.g., individual farms) located far from a biogas grid or natural gas grid. For example, since the biogas may be collected in its raw or partially purified form, there may be lower investment costs for the biogas producer (e.g., biogas upgrading investments are not required). Moreover, in embodiments where the biogas is subject to a partial purification that removes $H_2O$ and $H_2S$, a less expensive technology may be used since complete $H_2S$ may be provided at the fuel production facility.

Since the raw or partially purified biogas that is transported may have a significant $CO_2$ content, the $CO_2$ advantageously may be used to produce the fuel or may be collected on a larger scale (e.g., for sequestration and/or for producing another product). For example, the $CO_2$ may be converted to CO or may be used directly used as a feedstock for the gas fermentation. Accordingly, more renewable carbon from the biomass is converted to fuel.

In general, the fuel production process (e.g., ethanol or RNG production) may be improved by using one or more of the approaches described herein to transport a higher mass of biogas (per delivery) and/or to avoid phase changes within the pressure vessel system. For example, in one embodiment, the process includes combining at least two of the following approaches: a) using a pressure vessel system having a nominal pressure rating less than 2000 psig (13.8 MPa) for each delivery; b) heating the biogas before and/or during the decanting process (e.g., adding more than 200 kWh of heat per delivery); c) extending the total decant time to over 1 or 2 hours per delivery; and d) removing more than 20%, 30%, 40% or 50% of the $CO_2$ from the raw biogas prior to delivery. In one embodiment, the process includes combining at least two of the following approaches: a) using a pressure vessel system having a nominal pressure rating less than 2000 psig (13.8 MPa) for each delivery; b) heating the biogas before and/or during the decanting process (e.g., adding more than 200 kWh of heat per delivery); and c) extending the total decant time to over 1 or 2 hours per delivery. Advantageously, by selecting the appropriate combination, the decant time for each delivery may be reduced to less than 2 or 3 hours. In one embodiment, the decant time for each delivery is under 3 hours, under 2.5 hours, under 2 hours, under 1.5 hours, or under 1 hour.

In one embodiment, the process includes a combination of using a pressure vessel system with a nominal pressure rating that is less than 2000 psig (6.9 MPa) and providing more than 200 kWh of heat per delivery. This embodiment may provide the advantage of reducing compression costs, while maximizing the mass of biogas transported and decreasing decanting time.

In one embodiment, the process includes a combination of using a pressure vessel system having a nominal pressure rating that is less than 2000 psig (6.9 MPa) and extending the total decant time to over 1 or 2 hours. This embodiment may provide the advantage of reducing compression costs, while maximizing the mass of biogas transported and decreasing heating costs.

In one embodiment, where the process uses a pressure vessel system having a nominal pressure rating greater than 2000 psig (6.9 MPa), the process includes a combination of providing more than 200 kWh of heat per delivery and extending the total decant time to over 1 or 2 hours. This embodiment may provide the advantage of being able to transport biogas at relatively high pressures while reducing risks associated with phase changes.

In one embodiment, the process includes a combination of removing at least 85% of the $CO_2$ in a partial purification, providing active and/or passive heating of the partially purified biogas in the pressure vessel system, and extending the total decant time to at least 40 minutes.

In one embodiment, the relatively high transport pressure is used to advance the fuel production process and/or a biogas upgrading process. For example, in one embodiment, the decanting process depressurizes the biogas from a relatively high pressure (e.g., above 2000 psig (6.9 MPa)) down to a final pressure that is greater than about 500 psig (3.4 MPa) (e.g., between 600 psig (4.1 MPa) and about 1200 psig (8.3 MPa). Since the final pressure is relatively high, the biogas can be fed at this high pressure directly to a process unit that uses and/or benefits from high pressure, without having to first compress the biogas. For example, some membrane units and/or absorption units can remove $CO_2$ more efficiently at high pressures.

Figure 7:
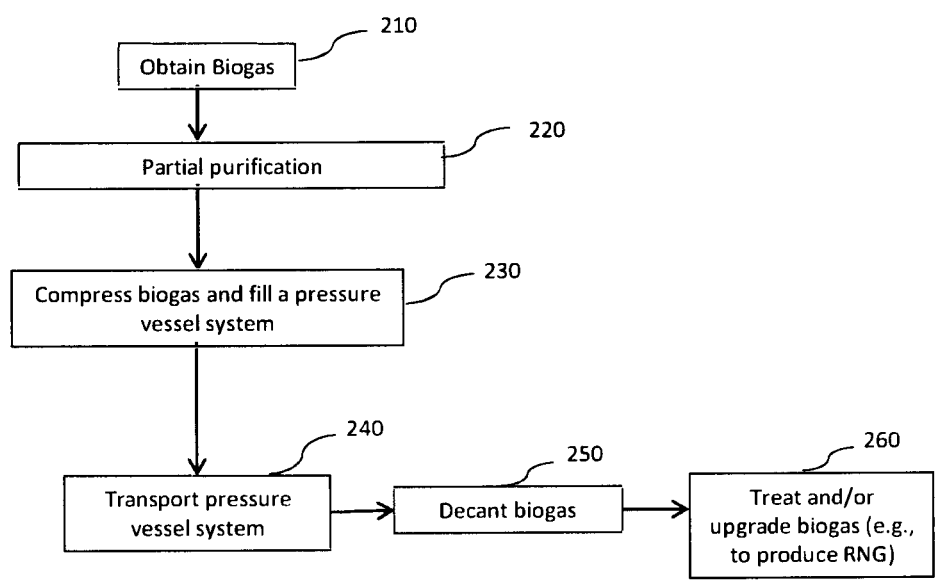
FIG. 7 is a flow diagram illustrating a method in accordance with an embodiment of the invention.

Referring to FIG. 7, there is shown an embodiment wherein the fuel produced is RNG. In this embodiment, the process includes the steps collecting raw biogas from a first biogas source 210, subjecting the raw biogas to a partial purification 220, compressing and filling a pressure vessel system with the partially purified biogas 230, transporting the compressed partially purified biogas to a receiving station 240, decanting the biogas 250, and treating and/or upgrading the partially purified biogas to produce RNG 260 and/or pipeline quality gas.

Example 1

The following example illustrates an embodiment of a decanting process that may be used in the process illustrated in FIG. 6 or 7. For the purposes of this example, the partial purification 220 removes $H_2O$ and $H_2S$, thereby providing a partially purified biogas having a $CH_4$ content of 50%, a $CO_2$ content of 38%, a $N_2$ content of 10%, and an $O_2$ content of 2% (on a mole basis). In this example, which is discussed with reference to FIGS. 8a-8c, the following parameters were used/assumed for the modelling. The loading step fills a pressure vessel system having a nominal pressure rating of 3600 psig (24.8 MPa) at 21° C. with biogas until the pressure reaches 4000 psig (27.6 MPa) and the temperature is about 50° C. The density of the biogas is 360 kg/m$^3$. By the time the filled pressure vessel system reaches the receiving station, the pressure and temperature have dropped to 3850 psig (26.5 MPa) and 44° C., respectively. The density does not change.

Figure 8A:
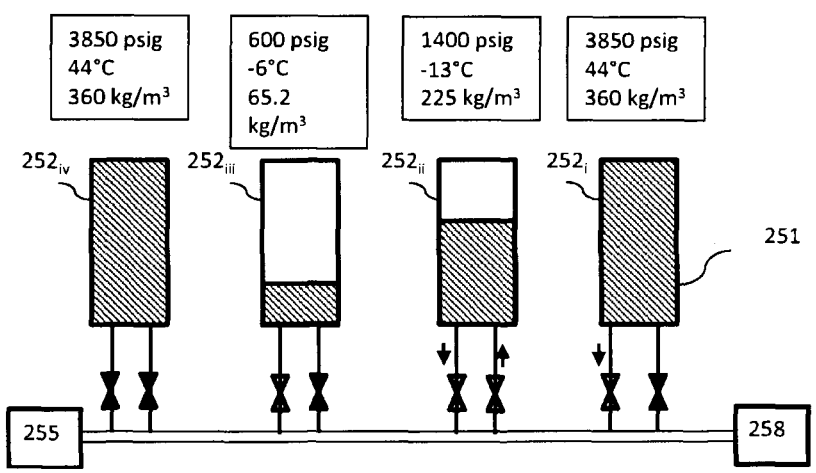
FIG. 8a is a schematic diagram illustrating a first stage of decanting process in accordance with one embodiment.
Figure 8B:
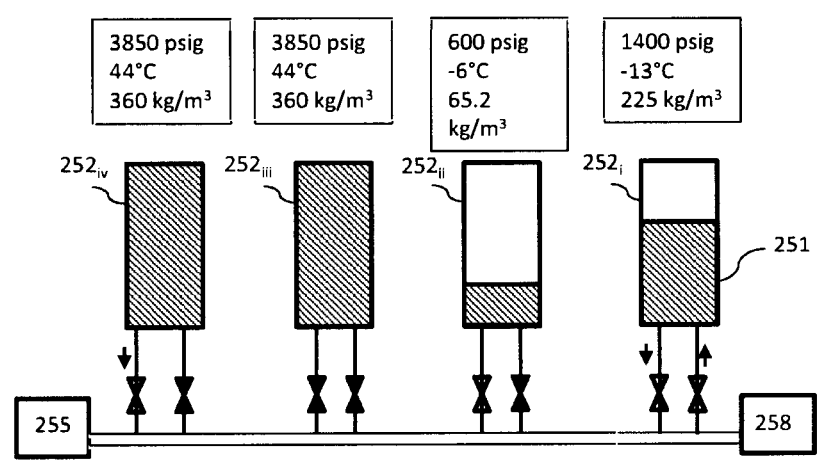
FIG. 8b is a schematic diagram illustrating a second stage of decanting process in accordance with one embodiment.
Figure 8C:
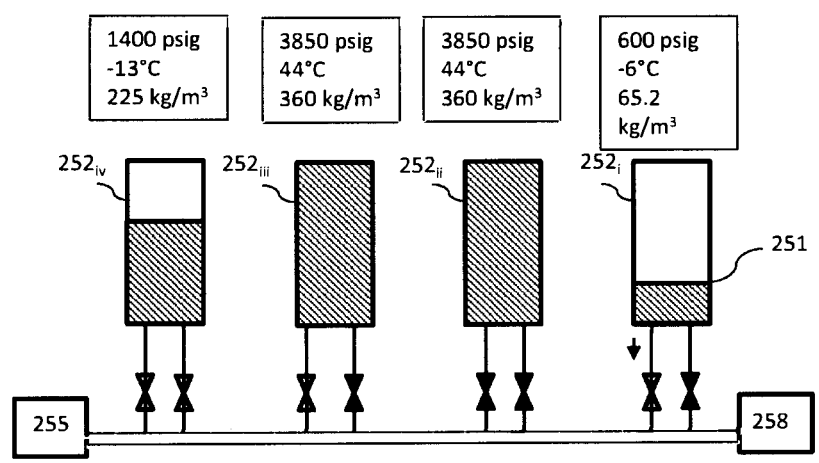
FIG. 8c is a schematic diagram illustrating a third stage decanting process in accordance with one embodiment.

Referring to FIGS. 8a-8c, the pressure vessel to be decanted 251 is docked at a receiving station having four bays 252$_i$, 252$_{ii}$, 252$_{iii}$, and 252$_{iv}$, each of which is configured to accommodate a shipping container/pressure vessel system. For illustrative purposes, the pressure vessel system in the first bay 252$_i$ is referred to as the first pressure vessel system, the pressure vessel system in the second bay 252$_{ii}$ is referred to as the second pressure vessel system, the pressure vessel system in the third bay 252$_{iii}$ is referred to as the third pressure vessel system, and the pressure vessel system in the fourth bay 252$_{iv}$ is referred to as the fourth pressure vessel system. Each of the pressure vessel systems, which are shown schematically with different fill levels, has two inlet/outlets. For illustrative purposes the docking stations are shown connected by a simplified manifold, however, as will be understood by those in the art, the interconnecting system, which may be simple or complex, will typically be designed in dependence upon the decanting process.

Before the decanting of the first pressure vessel system 251 starts, the first pressure vessel system is at 3850 psig (26.5 MPa) and 44° C. The density of this biogas is about 360 kg/m$^3$. The second pressure vessel system, which has already had some of the biogas removed, is at 1400 psig (9.7 MPa) and -13° C. The density of this biogas is about 225 kg/m$^3$. The first pressure vessel system is decanted in three stages. The start of each stage is illustrated in FIGS. 8a, 8b, and 8c, respectively.

In the first stage of the decanting process (e.g., see FIG. 8a), the biogas in the first pressure vessel system is depressurized from 3850 psig (26.5 MPa) to 1400 psig (9.7 MPa) through the second pressure vessel system. More specifically, a stream of biogas is withdrawn from the first pressure vessel system 251, is heated by a heat exchanger (not shown) to 80° C. and fed into the second pressure vessel system. Since the two pressure vessel systems are at different pressures, the transfer may be pressure driven. As the relatively warm biogas is enters the second pressure vessel system, the contents therein are warmed. As the relatively warm biogas is fed into the inlet of second pressure vessel system, the contents of the second pressure vessel system are simultaneously removed from the outlet of the second pressure vessel system and fed to a pressure let down system 255. Accordingly, the biogas decanted from the second pressure vessel system is a mixture of the two biogases. Once the pressure of the first pressure vessel system reaches 1400 psig (9.7 MPa) and about -13° C., the inlet/outlet valves are adjusted.

In the second stage of the decanting process (e.g., see FIG. 8b), the first pressure vessel system is decanted down to 600 psig, as a relatively warm gas from the fourth pressure vessel system (i.e., at 3850 psig (26.5 MPa) and 44° C.) is simultaneously injected. More specifically, a stream of biogas is withdrawn from the fourth pressure vessel system, is heated by a heat exchanger (not shown) to 80° C. and fed into the first pressure vessel system as it is depressurized down to 600 psig (4.1 MPa). Since the two pressure vessel systems are at different pressures, the transfer may be pressure driven. Advantageously, the heat added into the first pressure vessel (i.e., the warmed biogas from the fourth pressure vessel system) keeps the contents of the first pressure vessel above -20° C. as it is depressurized down to 600 psig (4.1 MPa). Further advantageously, the warmed biogas creates an aggregate of two biogases. Once the pressure of the fourth pressure vessel system reaches 1400 psig (9.7 MPa), the inlet/outlet valves are adjusted. At the end of this stage, about 90% of the biogas from the first pressure vessel system has been removed (i.e., density is 65.2 kg/m$^3$) and the temperature is -6° C. Advantageously, the aggregate biogas removed during the first and second stages by the pressure let down system 255 may be provided at a constant flow rate (mass) and/or at 600 psig (4.1 MPa), without compression.

In a third stage of the process, the first pressure vessel system is decanted down to 200 psig (1.4 MPa). Advantageously, the biogas removed during the third stage may be fed to another pressure let down system 258, which is controlled to provide biogas at a lower pressure (e.g., 200 psig (1.4 MPa)), or may be fed to a compressor to provide biogas at a higher pressure (e.g., 600 psig (4.1 MPa)). Advantageously, since this biogas can reach lower temperatures at these relatively low pressures (e.g., below 600 psig (4.1 MPa)) without approaching the dew line, it may not be necessary to heat the biogas during the third stage.

In this example, the biogas in the first and second stages is provided at 600 psig (4.1 MPa), however, it may be advantageous to select the pressure in dependence upon subsequent processing units. In particular, if the biogas is fed to one or more processing units, the pressure let down pressure may be selected accordingly. For example, membranes, which are typically more efficient at higher pressures, may benefit from feed gas up to 1200 psig, whereas SMR units may be operated at pressures between 200 psig (1.4 MPa) and 600 psig (4.1 MPa) and ATR reactors may be operated at pressures between 430 psig (3.0 MPa) and 1000 psig (6.9 MPa). In one embodiment, at least a portion of the unloaded biogas is provided at a let down pressure of at least 500 psig (3.4 MPa), at least 600 psig (4.1 MPa), at least 700 psig (4.8 MPa), at least 800 psig (5.5 MPa), at least 900 psig (6.2 MPa), at least 1000 psig (6.9 MPa), at least 1100 psig (7.6 MPa), or at least 1200 psig (8.3 MPa). In one embodiment, another portion of the biogas, which is at a lower pressure, is used at the lower pressure or is compressed to the higher pressure.

Referring again to FIGS. 8a-c, the decanting process allows each of the docking stations to cycle between different stages. For example, at any point in time one docking station will be connected to a pressure vessel system in the first stage, another docking station will be connected to a pressure vessel system in the second stage, and yet another docking station will be connected to a pressure vessel system in the third stage. A fourth docking station may be used as a queue, a back-up, and/or for preheating pressure vessel systems (e.g., with a heating loop). For example, the fourth docking station may be used to preheat biogas to 44° C. in cases where it falls below an acceptable level (e.g., in some winter climates).

Advantageously, this decanting process allows the pressure let down system 255 to receive a continuous flow of biogas from pressure vessel systems in the second stage. For example, the pressure let down system 255 will alternatingly receive biogas from the second pressure vessel system (FIG. 8a), the first pressure vessel system (FIG. 8b), the fourth pressure vessel system (FIG. 8c), and the third pressure vessel system (not shown).

At the same time, another pressure let down system 258 may receive a continuous flow of biogas from pressure vessel systems in the third stage. For example, the pressure let down system 258 will alternatingly receive biogas from the third pressure vessel system (FIG. 8a), the second pressure vessel system (FIG. 8b), the first pressure vessel system (FIG. 8c), and the fourth pressure vessel system (not shown). Accordingly, in addition to the flexibility of providing the biogas at two different pressures, there can be reduced compression costs and/or reduced total decant time (e.g., with reduced risk of phase change).

The decanted biogas is fed to fuel production (e.g., to a biogas upgrading facility for producing RNG (e.g., bio-CNG or bio-LNG)). Advantageously, the above described configuration allows about 90% of the biogas to be fed to fuel production at a higher pressure, without additional compression. The remaining 10%, which is at lower pressure, may be compressed and also fed to the fuel production as feedstock, or may be used at the lower pressures for heat and/or power generation for the fuel production process (e.g., without upgrading).

The decanting process described with reference to FIGS. 8a to 8c can improve fuel production (e.g., RNG production and/or fuel production using methane reforming). For example, in one embodiment, the biogas at a higher pressure is used as feed to a methane reformer (e.g., with or without further purification), while the biogas at the lower pressure is used as fuel for the methane reformer.

Advantageously, since the fuel is produced from partially purified biogas obtained from a plurality of biogas sources, the fuel production facility may be a relatively large scale facility and may profit from the economies of scale. For example, $N_2$ removal may be relatively costly on a small scale, but may be justifiable on a larger scale. Accordingly, a higher quality RNG may be provided.

Further advantageously, the fuel production process may benefit from the pressurization of biogas. Various biogas upgrading technologies are emerging and/or being developed that benefit from high pressure feeds (e.g., greater than 200 psig (1.4 MPa)). However, since it can be expensive to compress biogas, such technologies may be overlooked and/or their use discouraged. However, in the above described embodiments, the relatively high pressure of the decanted biogas can be exploited, thereby reducing compression costs. This synergetic benefit may improve the biogas upgrading process and/or fuel production process.

In one embodiment, the relatively high pressure of the biogas is used to improve the process and/or make the biogas upgrading more economical. For example, in one embodiment, the depressurization is used to boost the pressure of another gas. This may reduce compression costs. For example, if the biogas upgrading includes a two stage membrane system that removes $CO_2$, the use of a compressor for the recycle stream may be obviated by using a venturi and the relatively high pressure of the biogas.

Example 2

Figure 9:
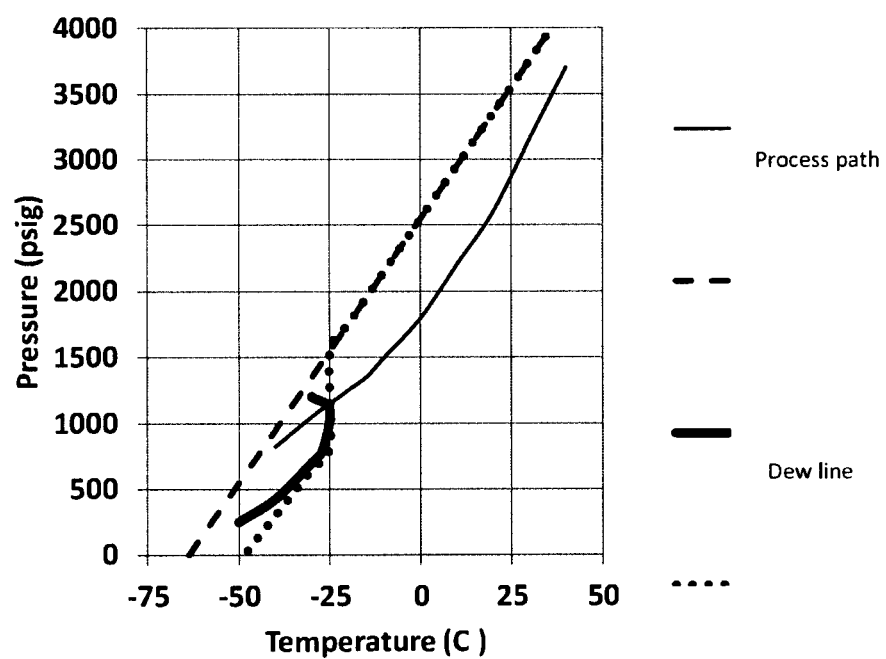
FIG. 9 is a plot of pressure versus temperature showing the modeled decanting of biogas.

Referring to FIG. 9, there is shown the calculated dew line for biogas having a $CH_4$ content of 50%, a $CO_2$ content of 38%, a $N_2$ content of 10%, and an $O_2$ content of 2%, where the dew line was simulated for the Peng-Robinson Equation of State, and where the property parameters are taken from Aspen HYSYS V9.

Also shown in FIG. 9 is the process path calculated for this biogas as it is decompressed from a pressure of 3850 psig (26.5 MPa) and 44° C. (i.e., without temperature and/or flow rate adjustments). The process path was calculated using the Peng-Robinson Equation of State, in Aspen. The simulations assume the vessel is about 1 cubic meter, has a height to diameter ratio of 4:1, and is decompressed at a uniform mass flow over 60 minutes. It also accounts for some heat transfer from the walls to the biogas, during winter conditions (i.e., ambient air is −20° C.).

As illustrated in FIG. 9, the biogas, which starts out in the gas phase, experiences a decrease in temperature as the pressure is reduced. By the time the pressure is reduced to about 1200 psig (8.3 MPa), it reaches the calculated dew line. Without adjusting the temperature and/or decanting flow rate, the process path will cross the calculated dew line (e.g., some of the biogas may liquefy at about −25° C. as it crosses the dew line).

In one embodiment, the risk of liquefaction is reduced by adjusting the decanting flow rate during the decanting process and/or heating the biogas during the decanting process. In one embodiment, this adjustment is initiated in dependence upon a measured temperature and/or pressure within the vessel being decanted, and in dependence upon the calculated dew line.

In one embodiment, the risk of liquefaction is reduced by providing sufficient heat such that the process path skirts at least a portion of the calculated dew line (e.g., within some margin, such as 5 or 10° C.). In one embodiment, this heat is provided by active heating (e.g., using a warming gas). In one embodiment, this heat is provided by passive heating (e.g., by providing a rest period during the decanting process to allow warm ambient air to heat the gas).

In one embodiment, the risk of liquefaction is reduced by providing sufficient heat such that the process path stays to the right of the dashed and/or dotted lines in FIG. 9. In one embodiment, this heat is provided by active heating (e.g., using a warming gas). In one embodiment, this heat is provided by passive heating (e.g., by providing a rest period during the decanting process to allow warm ambient air to heat the gas).

The dashed line illustrated in FIG. 9 corresponds to:

$$P(psig) = 40T(° \text{ C.}) + 2550 (\text{e.g., where } T \geq -63.75° \text{ C.})$$

In one embodiment, the risk of liquefaction is reduced by providing sufficient heat such that the temperature of the biogas in the pressure vessel, in degrees Celsius, is greater than $$\frac{P(\text{in }psig) - 2550}{40}$$

This embodiment may be particularly advantageous for partially purified biogas containing primarily $CH_4$, $CO_2$, $N_2$, and/or $O_2$, particularly when the $CO_2$ content is at least 6%, at least 7%, at least 8%, at least 9%, or at least 10%. For example, according to modeling results, it may be suitable for biogas compositions containing 76.6% $CH_4$, 6.9% $CO_2$, 13.75% $N_2$, and 2.75% $O_2$, and for biogas compositions containing 50% $CH_4$, 38% $CO_2$, 10% $N_2$, and 2%.

In one embodiment, the risk of liquefaction is reduced by providing sufficient heat such that the temperature of the biogas in the pressure vessel, in degrees Celsius, is greater than $$\frac{P(\text{in }psig) - 2550}{40}$$

where the composition of the biogas is such that $CH_4$, $CO_2$, and $N_2$ make up at least 90% of the gas mixture (e.g., by volume).

In one embodiment, the risk of liquefaction is reduced by providing sufficient heat such that the temperature of the biogas in the pressure vessel, in degrees Celsius, is greater than $$\frac{P(\text{in }psig) - 2550}{40}$$

for pressures greater than 1550 psig (10.7 MPa). For example, for in this case, when the pressure is 3000 psig (20.7 MPa), the temperature should be greater than 11° C., whereas when the pressure is 1550 psig (10.7 MPa), the temperature should be greater than −25° C.

In one embodiment, the risk of liquefaction is reduced by providing sufficient heat such that the temperature of the biogas in the pressure vessel, in degrees Celsius, is greater than $$\frac{(P(\text{in }MPa) * 145.04) - 2550}{40}$$

(e.g., for pressures greater than 10.7 MPa and/or when the composition of the biogas is such that $CH_4$, $CO_2$, and $N_2$ make up at least 90% of the gas mixture (e.g., by volume)).

The lower dotted line illustrated in FIG. 9 corresponds to:

$$P(psig) = 35T(° C.) + 1700 (\text{e.g., where} - 48.6 \le T \le -25° C.)$$

In one embodiment, the risk of liquefaction is reduced by providing sufficient heat such that the temperature of the biogas in the pressure vessel, in degrees Celsius, is greater than $$\frac{P(\text{in }psig) - 1700}{35}$$

for pressures less than 825 psig and greater than 0 psig. For example, for in this case, when the pressure is about 500 psig, the temperature could be as low as −34° C., whereas when the pressure is about 200 psig, the temperature could be as low as −42° C.

In one embodiment, the risk of liquefaction is reduced by providing sufficient heat such that the temperature of the biogas in the pressure vessel is greater than $$\frac{P(\text{in }psig) - 1700}{35}$$

for pressures less than 825 psig and greater than 0 psig (e.g., where the pressure in the equation is in psig) and greater than −25° C. for pressures greater than 825 psig.

In one embodiment, the risk of liquefaction is reduced by providing sufficient heat such that the temperature of the biogas in the pressure vessel, in degrees Celsius, is greater than $$\frac{(P(\text{in }MPa) * 145.04) - 1700}{35}$$

for pressures less than 5.7 MPa and greater than 0 MPa, or for pressures less than 5.7 MPa and greater than 0 MPa and greater than −25° C. for pressures greater than 5.7 MPa.

In one embodiment, the risk of liquefaction is reduced by providing sufficient heat such that the temperature of the biogas in the pressure vessel is:
  ≥P(in psig)−2550/40 for pressures greater than 1550 psig;
  ≥−25° C. for pressures between 825 psig and 1550 psig; and is
  ≥P(in psig)−1700/35 for pressures less than 825 psig and greater than 0 psig.

In one embodiment, the risk of liquefaction is reduced by providing sufficient heat such that the temperature of biogas within the pressure vessel is greater than −25° C., greater than −20° C., or greater than −15° C. at pressures between 900 psig (6.2 MPa) and 1100 psig (7.6 MPa). In one embodiment, the risk of liquefaction is reduced by providing sufficient heat such that the temperature of biogas within the pressure vessel is greater than −25° C., greater than −20° C., or greater than −15° C. at pressures between 900 psig (6.2 MPa) and 1100 psig (7.6 MPa).

In general, when heat is added and/or the decanting rate is controlled in dependence upon a measured temperature, the temperature will be measured so as to reflect the colder temperatures within a pressure vessel. In one embodiment, the temperature of biogas within the pressure vessel system is measured using a temperature sensor located within a pressure vessel, disposed near the bottom of the pressure vessel (e.g., where colder gas may be found). In one embodiment, the temperature is measured in a pipe or other conduit carrying the biogas out of the pressure vessel, where the biogas is withdrawn from a bottom half of the pressure vessel (e.g., where colder gas may be found). In one embodiment, the temperature of biogas within the pressure vessel system is measured using a temperature sensor located on an external wall of a pressure vessel, disposed near the bottom of the pressure vessel (e.g., where colder gas may be found).

In this embodiment, the external temperature is converted to an internal temperature (i.e., of the biogas within the pressure vessel) using a predetermined calibration. Without being limiting, the temperature sensor may be a thermocouple or resistance temperature detector.

Of course, the above embodiments have been provided as examples only. It will be appreciated by those of ordinary skill in the art that various modifications, alternate configurations, and/or equivalents will be employed without departing from the spirit and scope of the invention. For example, the receiving station configurations and pressure examples are provided for illustrative purposes, other configurations and/or pressures are possible and within the scope of the invention. Furthermore, although the various embodiments are described with reference to biogas, the methods and systems described herein can be used for any $CO_2/CH_4$ mixture, and in some cases for any gas. Although the various embodiments may be described with regard to decanting, transferring, heating, adding, etc. a "gas", as used herein, this term includes supercritical mixtures. Accordingly, the scope of the invention is therefore intended to be limited solely by the scope of the appended claims.

The invention claimed is:

1. A method of producing renewable fuel comprising:
a) receiving a plurality of pressure vessel systems, said plurality of pressure vessel systems comprising a first pressure vessel system containing a first biogas having a first density and a second pressure vessel system containing a second biogas having a second density;
b) providing fluid communication between the first pressure vessel system and a first valve and between the second pressure vessel system and a second other valve, each of said first and second valves in fluid communication with a same pressure let down system;
c) unloading the first and second biogases from the first and second pressure vessel systems, respectively, wherein said unloading comprises actuating the first and second valves such that the pressure let down system receives biogas from the first and second pressure vessel systems in succession before the first biogas is fully unloaded from the first pressure vessel system; and
d) feeding at least a portion of first and second biogases unloaded in step (c) into a biogas upgrading system, a fuel production process, or a combination thereof.

2. The method according to claim 1, wherein unloading the first biogas from the first pressure vessel system comprises feeding at least a portion of first biogas to the pressure let down system through the second pressure vessel system.

3. The method according to claim 1, wherein unloading the first biogas from the first pressure vessel system comprises feeding a first portion of the first biogas to the pressure let down system, and a second other portion of the first biogas to a second other pressure let down system, where the first pressure let down system provides the first biogas at a higher pressure than the second other let down system.

4. The method according to claim 1, wherein actuating the first and second valves is performed in dependence upon a measured pressure, temperature, mass, or any combination thereof.

5. The method according to claim 1, wherein actuating the first and second valves is performed in dependence upon a calculated dew line for the first biogas.

6. The method according to claim 1, wherein actuating the first and second valves is performed when the first pressure vessel system is between 80% full and 20% full by weight.

7. The method according to claim 1, wherein actuating the first and second valves is performed when at least 25% of the first biogas by weight has been removed from the first pressure vessel system.

8. The method according to claim 1, wherein each of the first and second densities is greater than 250 $kg/m^3$.

9. The method according to claim 1, wherein each of the first and second densities is greater than 300 $kg/m^3$.

10. The method according to claim 1, wherein each of the first and second densities is greater than 1.25 times a design density of natural gas.

11. The method according to claim 1, wherein actuating the first and second valves is performed in dependence upon a measured temperature of biogas within the first pressure vessel system, biogas within the second pressure vessel system, or a combination thereof.

12. The method according to claim 1, wherein step (c) comprises heating the first biogas in a pressure vessel of the first pressure vessel system.

13. The method according to claim 1, wherein each of the first and second biogases received in a) comprises raw biogas.

14. The method according to claim 1, wherein each of the first and second biogases received in a) has a carbon dioxide content of at least 5%.

15. The method according to claim 1, wherein d) comprises feeding at least a portion of first and second biogases unloaded in step (c) into the biogas upgrading system.

16. The method according to claim 15, wherein the fuel comprises renewable natural gas.

17. The method according to claim 1, wherein the fuel comprises hydrogen, methanol, ethanol, butanol, gasoline, diesel, dimethyl ether (DME), methyl tertiary butyl ether (MTBE), or any combination thereof.

18. The method according to claim 1, wherein d) comprises feeding at least a portion of first and second biogases unloaded in step (c) into the fuel production process, wherein the fuel production process comprises methane reforming.

19. The method according to claim 1, wherein the first and second densities are substantially the same.

20. A method of producing renewable fuel comprising:
a) receiving a plurality of pressure vessel systems, said plurality of pressure vessel systems comprising a first pressure vessel system containing a first biogas having a first density and a second pressure vessel system containing a second biogas having a second density;
b) providing fluid communication between the first pressure vessel system and a first valve and between the second pressure vessel system and a second other valve, each of said first and second valves in fluid communication with a pressure let down system;
c) unloading the first and second biogases from the first and second pressure vessel systems, respectively, wherein said unloading comprises actuating the first and second valves such that while unloading each of the first and second pressure vessel systems a first portion of the respective biogas is provided from a first pressure let down system at a pressure above 3.4 MPa, and a second portion is provided from a second other pressure let down system at a pressure below 3.4 MPa; and
and
d) feeding the first and second biogases unloaded in step (c) into a biogas upgrading system, a fuel production process, or a combination thereof.

* * * * *